(12) United States Patent
Doumbouya et al.

(10) Patent No.: US 10,776,672 B2
(45) Date of Patent: Sep. 15, 2020

(54) SENSOR FUSION FOR MONITORING AN OBJECT-OF-INTEREST IN A REGION

(71) Applicant: Avigilon Corporation, Vancouver (CA)

(72) Inventors: Moussa Doumbouya, Melrose, MA (US); Yanyan Hu, Medford, MA (US); Kevin Piette, Carlisle, MA (US); Pietro Russo, Melrose, MA (US); Mahesh Saptharishi, Boston, MA (US); Bo Yang Yu, Winchester, MA (US)

(73) Assignee: Avigilon Corporation, Vancouver (CA)

( * ) Notice: Subject to any disclaimer, the term of this patent is extended or adjusted under 35 U.S.C. 154(b) by 85 days.

(21) Appl. No.: 16/265,731

(22) Filed: Feb. 1, 2019

(65) Prior Publication Data
US 2019/0332901 A1 Oct. 31, 2019

Related U.S. Application Data

(60) Provisional application No. 62/662,639, filed on Apr. 25, 2018.

(51) Int. Cl.
*H04N 13/204* (2018.01)
*G06K 9/62* (2006.01)
(Continued)

(52) U.S. Cl.
CPC .......... *G06K 9/6289* (2013.01); *A61B 5/0077* (2013.01); *A61B 5/015* (2013.01); *A61B 5/0816* (2013.01); *A61B 5/746* (2013.01); *G01S 13/04* (2013.01); *G06K 9/00771* (2013.01); *G06T 7/20* (2013.01); *G06T 7/292* (2017.01); *G06T 7/593* (2017.01); *G06T 7/70* (2017.01); *G08B 21/182* (2013.01); *H04N 5/2253* (2013.01);
(Continued)

(58) Field of Classification Search
USPC ........................................................ 348/46
See application file for complete search history.

(56) References Cited

U.S. PATENT DOCUMENTS 7,929,017 B2 4/2011 Aggarwal et al.
8,174,572 B2 5/2012 Buehler et al.
(Continued)

FOREIGN PATENT DOCUMENTS

CN 103971359 A 8/2014
EP 1563686 B1 1/2010

OTHER PUBLICATIONS

International Search Report dated Jul. 3, 2019 issued on corresponding International Application No. PCT/CA2019/050478, 4 pages.
(Continued)

*Primary Examiner* — Nguyen T Truong
(74) *Attorney, Agent, or Firm* — Daniel Hammond

(57) ABSTRACT

Methods, systems, and techniques for monitoring an object-of-interest within a region involve receiving at least data from two sources monitoring a region and correlating that data to determine that an object-of-interest depicted or represented in data from one of the sources is the same object-of-interest depicted or represented in data from the other source. Metadata identifying that the object-of-interest from the two sources is the same object-of-interest is then stored for later use in, for example, object tracking.

20 Claims, 12 Drawing Sheets

(51) Int. Cl.
*G06T 7/593* (2017.01)
*G06K 9/00* (2006.01)
*G08B 21/18* (2006.01)
*G01S 13/04* (2006.01)
*A61B 5/01* (2006.01)
*A61B 5/08* (2006.01)
*A61B 5/00* (2006.01)
*G06T 7/20* (2017.01)
*G06T 7/292* (2017.01)
*G06T 7/70* (2017.01)
*H04N 5/225* (2006.01)

(52) U.S. Cl.
CPC ........ *H04N 13/204* (2018.05); *A61B 2576/00* (2013.01); *G06K 2209/27* (2013.01); *G06T 2207/10012* (2013.01); *G06T 2207/10021* (2013.01); *G06T 2207/10044* (2013.01); *G06T 2207/10048* (2013.01); *G06T 2207/20084* (2013.01); *G06T 2207/20212* (2013.01); *G06T 2207/30196* (2013.01); *G06T 2207/30232* (2013.01); *G06T 2207/30242* (2013.01)

(56) References Cited

U.S. PATENT DOCUMENTS

| | | |
|---|---|---|
| 8,284,254 B2 | 10/2012 | Romanowich et al. |
| 8,332,063 B2 | 12/2012 | Moshier |
| 8,731,239 B2 | 5/2014 | Gefen |
| 9,355,310 B2 | 5/2016 | Carbonell et al. |
| 9,615,064 B2 | 4/2017 | Millar et al. |
| 9,664,510 B2 | 5/2017 | Nathan et al. |
| 9,801,024 B2 | 10/2017 | Saleem |
| 2006/0028552 A1* | 2/2006 | Aggarwal .......... G06K 9/00295 348/169 |
| 2012/0154117 A1* | 6/2012 | Nice .................. G06K 9/00892 340/5.82 |
| 2013/0222599 A1 | 8/2013 | Shaw |
| 2014/0327780 A1 | 11/2014 | Herrli Anderegg et al. |
| 2014/0328512 A1 | 11/2014 | Gurwicz et al. |
| 2016/0274743 A1 | 9/2016 | Sica et al. |
| 2016/0292885 A1 | 10/2016 | Greenspan et al. |
| 2017/0076508 A1 | 3/2017 | VanBlon et al. |
| 2017/0154424 A1 | 6/2017 | Uchiyama et al. |
| 2017/0286730 A1* | 10/2017 | Sadr ......................... G01S 5/30 |
| 2018/0101960 A1 | 4/2018 | Boonyasiriwat et al. |
| 2018/0157939 A1 | 6/2018 | Butt et al. |
| 2019/0019017 A1 | 1/2019 | Wang et al. |
| 2019/0294889 A1 | 9/2019 | Sriram et al. |

OTHER PUBLICATIONS

Qognify Ltd., "Suspect search: when time is of the essence", Data sheet, 2015, 4 pages.

* cited by examiner

SENSOR FUSION FOR MONITORING AN OBJECT-OF-INTEREST IN A REGION

RELATED APPLICATION DATA

The present application claims the priority of U.S. provisional patent application No. 62/662,639 filed Apr. 25, 2018 and entitled "METHOD AND SYSTEM FOR MONITORING AN OBJECT-OF-INTEREST IN A REGION", the entire contents of which are herein incorporated by reference.

TECHNICAL FIELD

The present disclosure relates to methods, systems, and techniques for monitoring an object-of-interest in a region.

BACKGROUND

Computer-implemented visual object classification, also called object recognition, pertains to classifying visual representations of real-life objects found in still images or motion videos captured by a camera. By performing visual object classification, each visual object found in the still images or motion video is classified according to its type (such as, for example, human, vehicle, and animal).

Surveillance systems typically employ video cameras or other image capturing devices or sensors to collect image data such as videos. In the simplest systems, images represented by the image data are displayed for contemporaneous screening by security personnel and/or recorded for later review after a security breach. In those systems, the task of detecting and classifying visual objects-of-interest is performed by a human observer. A significant advance occurs when the system itself is able to perform object detection and classification, either partly or completely.

In a typical surveillance system, one may be interested in, for example, detecting objects such as humans, vehicles, and animals that move through the environment. More generally, it is beneficial for a surveillance system to be able to, without relying on assistance from a human operator, identify and classify, in a computationally efficiently manner, different objects that are recorded by the cameras that form part of the system. It may also be beneficial for a surveillance system to be able to monitor objects as they move in a region.

SUMMARY

According to a first aspect, there is provided a method comprising: receiving image data depicting an object-of-interest within a region and non-image data representing the object-of-interest within the region; determining that the object-of-interest depicted in the image data is the object-of-interest represented in the non-image data by correlating the image and non-image data; and storing metadata identifying the object-of-interest depicted in the image data and the object-of-interest represented in the non-image data as the same object-of-interest.

The method may further comprise: determining from at least one of the image and non-image data whether the object-of-interest satisfies an event threshold; and indicating that the object-of-interest satisfies the event threshold when the object-of-interest is determined to satisfy the event threshold.

Indicating that the object-of-interest satisfies the event threshold may comprise at least one of displaying and sounding an event notification.

The image data and the non-image data may collectively represent the object-of-interest at two locations at two different times, and the method may further comprise displaying, on a display, a tracking indicator indicating that the object-of-interest has moved between the two locations.

The tracking indicator may comprise a path indicator showing a path the object-of-interest has traveled between the two locations.

The method may further comprise using the non-image data to determine the two locations of the object-of-interest.

The method may further comprise determining, using the non-image data, biometric metadata associated with the object-of-interest using the non-image data.

The method may further comprise displaying, on a display, the biometric metadata, the image data depicting the object-of-interest that is associated with the biometric metadata, and an indication that the biometric metadata and the image data depicting the object-of-interest that is associated with the biometric metadata are associated.

The object-of-interest may be a person, the non-image data may comprise position metadata collected from a radar sensor, determining the biometric metadata may comprise determining a rate-of-respiration of the person, and the method may further comprise: determining whether the rate-of-respiration is below a minimum threshold; and when the rate-of-respiration is below the minimum threshold, triggering a rate-of-respiration alarm.

The object-of-interest may be a person, the image data may comprise thermal data, determining the biometric metadata may comprise determining a temperature of the person, and the method may further comprise: determining whether the temperature is within a temperature range; and when the temperature is outside of the temperature range, triggering a temperature alarm.

The method may further comprise determining position metadata using the non-image data.

The image data may be stereoscopic, and the method may further comprise determining depth metadata using the image data.

The image data may be of visible light images.

The non-image sensor may be selected from the group consisting of a radiofrequency radiation sensor, an ultra-wideband signal sensor, a depth sensor, an ultrasound sensor; a Hall Effect sensor, a mechanical switch, a six degree-of-freedom sensor, a nine degree-of-freedom sensor, an air quality sensor, a temperature sensor, a humidity sensor, a luminosity sensor, a water level sensor, a water pH sensor, an ionizing radiation sensor, a seismic sensor, a noise level sensor, a microwave radiation sensor, a radar sensor, a sensor for light in the Terahertz range, and a millimeter wave radiation sensor.

The image sensor may be selected from the group consisting of a visible light sensor, an ultraviolet light sensor, an infrared light sensor, a near infrared light sensor, a short-wavelength infrared light sensor, a mid-wavelength infrared light sensor, and a long-wavelength infrared light sensor.

The image data may be of a field-of-view, the non-image data may be of a scanning region, and the field-of-view and the scanning region may not overlap.

The image data may be of a field-of-view, the non-image data may be of a scanning region, and the field-of-view and the scanning region may overlap.

The region may comprise an interior of a room, and the each of the first and the second non-image sensor may be mounted on a ceiling of the room.

The non-image data may be generated using a radar sensor mounted to detect a crossing past a threshold distance from a doorway of the room, and the method may further comprise: using the non-image data from the radar sensor to determine when the object-of-interest has entered the room beyond the threshold distance; and when the object-of-interest has entered the room beyond the threshold distance, incrementing a count of a number of persons in the room.

The method may further comprise: using the non-image data from the radar sensor to determine when the object-of-interest has transitioned from, relative to the doorway, being outside of the threshold distance to within the threshold distance; and when the object-of-interest has transitioned, decrementing the count of the number of persons in the room.

The image data may be generated using a camera, the non-image data may be generated using a non-image capture device, and the camera may comprise a hub for the non-image capture device.

The method may comprise transmitting data from the non-image capture device via the hub.

The method may further comprise transmitting power to the non-image capture device via the hub.

The image and the non-image data may be substantially spatially correlated, and correlating the image and the non-image data may be performed using a convolutional neural network.

A first and a second non-image sensor may be used to generate the non-image data representing a first and a second location, respectively, of the object-of-interest within the region at two different times; and a first and a second image sensor may be used to generate the image data depicting the first and the second location, respectively, of the object-of-interest.

The method may further comprise depicting, on a display, a tracking indicator indicating that the object-of-interest has moved between the first and the second location.

Depicting the tracking indicator may comprise displaying, on the display: a first and a second field-of-view captured by the first and the second image sensor, respectively, wherein the first location is in the first field-of-view and the second location is in the second field-of-view; a first and a second bounding box around the object-of-interest at the first and the second location, respectively; and a correlation indicator in the first and the second field-of-view indicating that the object-of-interest displayed at the first location is identical to the object-of-interest displayed at the second location.

The image data may be output by an image capture device comprising the image sensor, the non-image data may be output by a non-image capture device comprising the non-image sensor, the image capture device may output a first object identifier associating the image sensor with the object-of-interest depicted in the image data, the non-image capture device may output a second object identifier associating the non-image sensor with the object-of-interest represented in the non-image data, correlating the image and non-image data may comprise mapping the first and second object identifiers to each other, and the method may further comprise determining the correlation indicator using the first and second object identifiers that have been mapped to each other.

The method may further comprise generating position metadata using the non-image data from the first and second non-image sensors, and depicting the tracking indicator may comprise displaying, on the display: a first and a second scanning region scanned by the first and the second non-image sensor, respectively, wherein the first location is in the first scanning region and the second location is in the second scanning region; and a path indicator depicting a path traveled by the object-of-interest determined using the position metadata, wherein the path indicator intersects the first and second locations.

The method may further comprise: displaying, on the display: an object-of-interest indicator along the path at the first location; a first field-of-view captured by the first image sensor, wherein the first location is in the first field-of-view; and a first bounding box around the object-of-interest at the first location; receiving a signal indicating the object-of-interest indicator is to move to the second location; and then displaying, on the display: the object-of-interest indicator along the path at the second location; a second field-of-view captured by the second image sensor, wherein the second location is in the second field-of-view; and a second bounding box around the object-of-interest at the second location.

The object-of-interest indicator at the first location may be concurrently displayed with the first bounding box, and the object-of-interest indicator at the second location may be concurrently displayed with the second bounding box.

The method may further comprise, prior to determining that the object-of-interest depicted in the image data is the object-of-interest represented in the non-image data by correlating the video and non-image data, receiving a signal to commence a search for the object-of-interest.

The image data may be output by an image capture device comprising an image sensor, the non-image data may be output by a non-image capture device comprising a non-image sensor, the image capture device may output a first object identifier associating the image sensor with the object-of-interest depicted in the image data, the non-image capture device may output a second object identifier associating the non-image sensor with the object-of-interest represented in the non-image data, and correlating the image and non-image data may comprise mapping the first and second object identifiers to each other.

According to another aspect, there is provided a system comprising: an image capture device; a non-image capture device; a processor communicatively coupled to the image and non-image capture devices; and a memory communicatively coupled to the processor and having stored thereon computer program code that is executable by the processor, wherein the computer program code, when executed by the processor, causes the processor to perform the method of any one of the foregoing aspects or suitable combinations thereof.

According to another aspect, there is provided a method comprising: receiving data from a first and a second sensor, wherein: the data comprises image data depicting an object-of-interest within a region, and each of the two sensors comprises an image sensor; or the data comprises non-image data representing the object-of-interest within the region, and each of the two sensors comprises a non-image sensor; determining that the object-of-interest depicted or represented in the data from the first sensor is the object-of-interest depicted or represented in the data from the second sensor by correlating the data from the first sensor with the data from the second sensor; and storing metadata identifying the object-of-interest depicted or represented in the data from the first sensor and the object-of-depicted or interest represented data from the second sensor as the same object-of-interest.

The data may comprise the non-image data. Alternatively, the data may comprise the image data.

The first sensor and the second sensor may return identical types, or different types, of non-image data.

According to another aspect, there is provided a system comprising: at least two image capture devices, or at least two non-image capture devices; a non-image capture device; a processor communicatively coupled to the image or non-image capture devices; and a memory communicatively coupled to the processor and having stored thereon computer program code that is executable by the processor, wherein the computer program code, when executed by the processor, causes the processor to perform the method of any of the foregoing aspects or suitable combinations thereof.

According to another aspect, there is provided a non-transitory computer readable medium having stored thereon computer program code that is executable by a processor and that, when executed by the processor, causes the processor to perform the method of any of the foregoing aspects or suitable combinations thereof.

This summary does not necessarily describe the entire scope of all aspects. Other aspects, features and advantages will be apparent to those of ordinary skill in the art upon review of the following description of example embodiments.

BRIEF DESCRIPTION OF THE DRAWINGS

In the accompanying drawings, which illustrate one or more example embodiments.

DETAILED DESCRIPTION

Figure 1:
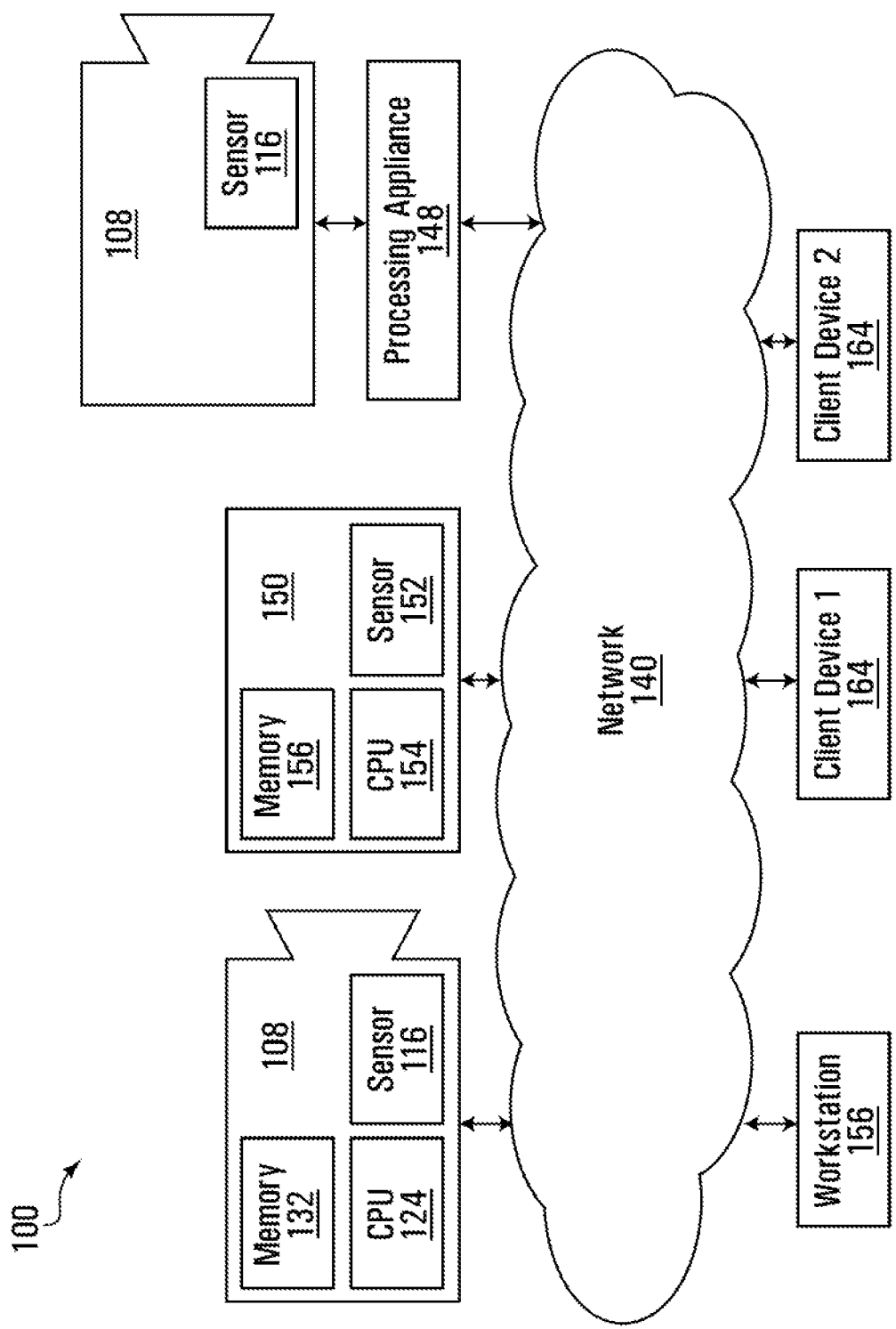
FIG. 1 illustrates a block diagram of connected devices of a data capture and playback system according to an example embodiment.

Numerous specific details are set forth in order to provide a thorough understanding of the example embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way but rather as merely describing the implementation of the various embodiments described herein.

The word "a" or "an" when used in conjunction with the term "comprising" or "including" in the claims and/or the specification may mean "one", but it is also consistent with the meaning of "one or more", "at least one", and "one or more than one" unless the content clearly dictates otherwise. Similarly, the word "another" may mean at least a second or more unless the content clearly dictates otherwise.

The terms "coupled", "coupling" or "connected" as used herein can have several different meanings depending in the context in which these terms are used. For example, the terms coupled, coupling, or connected can have a mechanical or electrical connotation. For example, as used herein, the terms coupled, coupling, or connected can indicate that two elements or devices are directly connected to one another or connected to one another through one or more intermediate elements or devices via an electrical element, electrical signal or a mechanical element depending on the particular context.

The term "and/or" herein when used in association with a list of items means any one or more of the items comprising that list.

The word "approximately" when used in conjunction with a number means, depending on the embodiment, that number itself, within 1% of that number, within 2% of that number, within 3% of that number, within 4% of that number, within 5% of that number, within 6% of that number, within 7% of that number, within 8% of that number, within 9% of that number, or within 10% of that number.

A plurality of sequential image frames may together form a video captured by an image capture device. Each image frame may be represented by a matrix of pixels, each pixel having a pixel image value. For example, the pixel image value may be a single numerical value for grayscale (such as, for example, 0 to 255) or a plurality of numerical values for colored images. Examples of color spaces used to represent pixel image values in image data include RGB, YUV, CYKM, YCBCR 4:2:2, YCBCR 4:2:0 images.

"Metadata" or variants thereof herein refers to information obtained by computer-implemented analyses and/or processing of image and/or non-image data, including video. For example, processing video may include, but is not limited to, image processing operations, analyzing, managing, compressing, encoding, storing, transmitting, and/or playing back the image data. Analyzing the video may include segmenting areas of image frames and detecting visual objects, and tracking and/or classifying visual objects located within the captured scene represented by the image data. The processing of the image data may also cause additional information regarding the image data or visual objects captured within the images to be output. That additional information is commonly referred to as "metadata". The metadata may also be used for further processing of the image data, such as drawing bounding boxes around detected objects in the image frames.

As will be appreciated by one skilled in the art, the various example embodiments described herein may be embodied as a method, system, or computer program product. Accordingly, the various example embodiments may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, the various example embodiments may take the form of a computer program product on a computer-usable storage medium having computer-usable program code embodied in the medium.

Any suitable computer-usable or computer readable medium may be utilized. The computer-usable or computer-readable medium may be, for example but not limited to, an electronic, magnetic, optical, electromagnetic, infrared, or semiconductor system, apparatus, device, or propagation medium. In the context of this document, a computer-usable or computer-readable medium may be any medium that can contain, store, communicate, propagate, or transport the program for use by or in connection with the instruction execution system, apparatus, or device.

Computer program code for carrying out operations of various example embodiments may be written in an object oriented programming language such as Java, Smalltalk, C++, Python, or the like. However, the computer program code for carrying out operations of various example embodiments may also be written in conventional procedural programming languages, such as the "C" programming language or similar programming languages. The program code may execute entirely on a computer, partly on the computer, as a stand-alone software package, partly on the computer and partly on a remote computer or entirely on the remote computer or server. In the latter scenario, the remote computer may be connected to the computer through a local area network (LAN) or a wide area network (WAN), or the connection may be made to an external computer (for example, through the Internet using an Internet Service Provider).

Various example embodiments are described below with reference to flowchart illustrations and/or block diagrams of methods, apparatus (systems) and computer program products according to example embodiments. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

Referring now to FIG. 1, therein illustrated is a block diagram of connected devices of a data capture and playback system 100 according to an example embodiment. For example, the data capture and playback system 100 may be used to capture image data, in which case it acts at least as a video surveillance system. The data capture and playback system 100 includes hardware and software that perform the processes and functions described herein.

The data capture and playback system 100 includes at least one image capture device 108 being operable to capture a plurality of images and produce image data representing the plurality of captured images. The image capture device 108 (hereinafter interchangeably referred to as a "camera 108") includes security video cameras.

Each image capture device 108 includes at least one image sensor 116 for capturing a plurality of images. The image capture device 108 may be a digital video camera and the image sensor 116 may output captured light as a digital data. For example, the image sensor 116 may be a CMOS, NMOS, or CCD sensor. In at least one different example embodiment (not depicted), the image capture device 108 may comprise an analog camera connected to an encoder, with the encoder digitizing analog video captured by the analog camera for subsequent processing.

In at least some example embodiments, the at least one image sensor 116 is configured to capture images in the visible light frequency range, which in at least some example embodiments is between about 400 nm to about 700 nm. However, the image capture device 108 need not be restricted to capturing visible light images; the image sensor 116 may additionally or alternatively be used to capture images using invisible light. For example, the image sensor 116 may additionally or alternatively be configured to capture images using any one or more of ultraviolet (UV) light; infrared (IR) light; near infrared (NIR) light; short-wavelength infrared (SWIR) light; medium or mid-wavelength infrared light (MWIR); and long-wavelength infrared light (LWIR) light. In at least some example embodiments, UV light comprises wavelengths selected from a range of approximately 10 nm to 400 nm; IR light comprises wavelengths selected from a range of approximately 400 nm to 1 mm; NIR light comprises wavelengths selected from a range of approximately 0.75 μm to 1.4 μm; SWIR light comprises wavelengths selected from a range of approximately 400 nm to 1 mm; MWIR light comprises wavelengths selected from a range of approximately 3 μm to 8 μm; and LWIR comprises wavelengths selected from a range of approximately 8 μm to 15 μm.

Data generated using the image sensor 116 is herein referred to as "image data". In FIG. 1, the image capture device 108 comprises a single image sensor 116 that is configured to capture light over the entire visible light frequency range; in at least some different example embodiments, the device 108 and/or the system 100 may comprise multiple sensors 116, with each of the sensors 116 configured to capture light spanning a different portion of the visible or invisible light frequency ranges.

The at least one image capture device 108 may include a dedicated camera. It will be understood that a dedicated camera herein refers to a camera whose principal feature is to capture images or video. In some example embodiments, the dedicated camera may perform functions associated to the captured images or video, such as but not limited to processing the image data produced by it or by another image capture device 108. For example, the dedicated camera may be a surveillance camera, such as any one of a pan-tilt-zoom camera, dome camera, in-ceiling camera, box camera, and bullet camera.

Additionally or alternatively, the at least one image capture device 108 may include an embedded camera. It will be understood that an embedded camera herein refers to a camera that is embedded within a device that is operational to perform functions that are unrelated to the captured image or video. For example, the embedded camera may be a camera found on any one of a laptop, tablet, drone device, smartphone, video game console or controller. More generally, the at least one image capture device 108 may include a combination device, which is any device comprising a camera and at least one additional device that has non-camera functionality, and in which the camera and at least one additional device are contained within a single housing or are otherwise suitably collocated. For example, an intercom that comprises a camera collocated within the same housing as a display and an audio transceiver is an example of a combination device.

In at least some example embodiments, the image capture device 108 may be a mobile device, examples of which include the laptop, tablet, drone device, and smartphone. The mobile device may have its own propulsion unit, such as the drone device; alternatively, the mobile device may lack a propulsion unit, such as the laptop, tablet, and smartphone.

Each image capture device 108 includes one or more processors 124, one or more memory devices 132 coupled to the processors and one or more network interfaces. The memory device can include a local memory (such as, for example, a random access memory and a cache memory) employed during execution of program instructions. The processor executes computer program instructions (such as, for example, an operating system and/or application programs), which can be stored in the memory device.

In various embodiments the processor 124 may be implemented by any suitable processing circuit having one or more circuit units, including a digital signal processor (DSP), graphics processing unit (GPU), embedded processor, etc., and any suitable combination thereof operating independently or in parallel, including possibly operating redundantly. Such processing circuit may be implemented by one or more integrated circuits (IC), including being implemented by a monolithic integrated circuit (MIC), an Application Specific Integrated Circuit (ASIC), a Field Programmable Gate Array (FPGA), etc. or any suitable combination thereof. Additionally or alternatively, such processing circuit may be implemented as a programmable logic controller (PLC), for example. The processor may include circuitry for storing memory, such as digital data, and may comprise the memory circuit or be in wired communication with the memory circuit, for example.

In various example embodiments, the memory device 132 coupled to the processor circuit is operable to store data and computer program code. Typically, the memory device is all or part of a digital electronic integrated circuit or formed from a plurality of digital electronic integrated circuits. The memory device may be implemented as Read-Only Memory (ROM), Programmable Read-Only Memory (PROM), Erasable Programmable Read-Only Memory (EPROM), Electrically Erasable Programmable Read-Only Memory (EEPROM), flash memory, one or more flash drives, universal serial bus (USB) connected memory units, magnetic storage, optical storage, magneto-optical storage, etc. or any combination thereof, for example. The memory device may be operable to store memory as volatile memory, non-volatile memory, dynamic memory, etc. or any combination thereof.

In various example embodiments, a plurality of the components of the image capture device 108 may be implemented together within a system on a chip (SOC). For example, the processor 124, the memory device 132 and the network interface may be implemented within a SOC. Furthermore, when implemented in this way, a general purpose processor and one or more of a GPU and a DSP may be implemented together within the SOC.

Continuing with FIG. 1, each of the at least one image capture device 108 is connected to a network 140. Each image capture device 108 is operable to output image data representing images that it captures and transmit the image data over the network.

In addition to the image capture device 108 depicted in FIG. 1, the system 100 also comprises at least one non-image capture device 150. The non-image capture device 150 comprises a non-image sensor 152, a processor 154, and a memory 156, with the sensor 152 and the memory 156 being communicatively coupled to the processor 154. The processor 154 and memory 156 comprising part of the non-image capture device 150 may, in at least some example embodiments, be selected from any of the processor 124 and memory 132 that are suitable for use in the image capture device 108, as discussed above. The sensor 152 comprising part of the non-image capture device 150 is a non-image sensor that captures data hereinafter referred to as "non-image data". For example, the non-image sensor 152 may be configured to capture data using radiofrequency (RF) radiation (e.g., Bluetooth™ and Wi-Fi™ signals for tracking phones and devices); an ultra-wideband signal sensor to measure location such as when using an ultra-wideband real-time location system (UWB RTLS); a depth sensor, such as a time-of-flight depth sensor which comprises part of a 3D camera; an ultrasound sensor; a Hall Effect sensor (e.g., a Reed Switch); a mechanical switch (e.g., a door contact); a six degree-of-freedom (6DOF) sensor; a nine degree-of-freedom (9DOF) sensor; an environmental sensor, such as an air quality sensor (e.g., for measuring particulates and specific gases such as carbon monoxide), a temperature sensor, a humidity sensor, a luminosity sensor, a water level sensor, a water pH sensor, an ionizing radiation sensor, seismic sensor, and a noise level sensor; microwave radiation; radar signals; light in the Terahertz range; and millimeter wave (mmWave) radar radiation. In at least some example embodiments, microwave radiation comprises wavelengths selected from a range of approximately 0.1 cm to 1 m; radar signals comprise wavelengths selected from a range of approximately 2.7 mm to 100 m and, more particularly, from approximately 0.75 cm to 1.1 cm; light in the Terahertz range comprises wavelengths selected from a range of approximately 100 um to 1 mm; and mmWave radiation comprises wavelengths selected from a range of approximately 1 mm to 1 cm.

In the example of a 3D camera, which captures visible light images concurrently with depth information, the 3D camera may comprise both the image sensor 116 for capturing image data (i.e., visible light images), and the non-image sensor 152 for capturing non-image data (i.e., time of flight information, which is used to generate metadata in the form of depth information); alternatively, the 3D camera may for example comprise a pair of image sensors 116, collect only image data in stereo, and analyze that stereo image data to generate metadata representing the depth information.

Various non-image data sensors may have different applications in different example embodiments. For example, a 3D camera may be used for 3D localization, people tracking applications (e.g., a camera may be configured to automatically focus, zoom in on, and/or count the number of people in its field-of-view once motion has been detected), and access control tailgating; data from thermal cameras, depth sensors, and/or radar sensors may be overlaid with image data; cameras may be configured to automatically focus and/or zoom in on an environmental anomaly detected by an environmental sensor; a radar sensor may be used for 3D localization and/or healthcare applications; and a 6DOF sensor may be used for access control.

It will be understood that the network 140 may be any suitable communications network that provides reception and transmission of data. For example, the network 140 may be a local area network, external network (such as, for example, WAN, Internet) or a combination thereof. In other examples, the network 140 may include a cloud network.

In some examples, the data capture and playback system 100 includes a processing appliance 148. The processing appliance 148 is operable to process the video and non-image data output by an image capture device 108 and a non-image capture device 150, respectively. The processing appliance 148 also includes one or more processors and one or more memory devices coupled to the one or more processors (CPU). The processing appliance 148 may also include one or more network interfaces. For convenience of illustration only one processing appliance 148 is shown; however it will be understood that the data capture and playback system 100 may include any suitable number of processing appliances 148.

For example, and as illustrated, the data capture and playback system 100 includes at least one workstation 156 (such as, for example, a server), each having one or more processors including graphics processing units (GPUs). The at least one workstation 156 may also include storage memory. The workstation 156 receives image and non-image data from at least one image capture device 108 and non-image capture device 150, respectively, and performs processing of that data. The workstation 156 may further send commands for managing and/or controlling one or more of the image capture devices 108 and non-image capture devices 150. The workstation 156 may receive raw image and non-image data from the image capture device 108 and non-image capture device 150, respectively. Alternatively or additionally, the workstation 156 may receive data that has already undergone some intermediate processing, such as processing at the image capture device 108, non-image capture device 150, and/or at a processing appliance 148. The workstation 156 may also receive metadata based on the image and/or non-image data and perform further processing of that data.

It will be understood that while a single workstation 156 is illustrated in FIG. 1, the workstation may be implemented as an aggregation of a plurality of workstations.

The data capture and playback system 100 further includes at least one client device 164 connected to the network 140. The client device 164 is used by one or more users to interact with the data capture and playback system 100. Accordingly, the client device 164 includes at least one display device and at least one user input device (such as, for example, a mouse, keyboard, and/or touchscreen). The client device 164 is operable to display on its display device a user interface for displaying information, receiving user input, and playing back video. For example, the client device may be any one of a personal computer, laptop, tablet, personal data assistant (PDA), cell phone, smart phone, gaming device, and other mobile device.

The client device 164 is operable to receive image data over the network 140 and is further operable to playback the received image data. A client device 164 may also have functionalities for processing image data. For example, processing functions of a client device 164 may be limited to processing related to the ability to playback the received image data. In other examples, image processing functionalities may be shared between the workstation and one or more client devices 164.

In some examples, the data capture and playback system 100 may be implemented without the workstation 156. Accordingly, image processing functionalities may be performed on a system entity other than the workstation 156 such as, for example, the image processing functionalities may be wholly performed on the one or more image capture devices 108. Alternatively, the image processing functionalities may be, for example, shared amongst two or more of the image capture device 108, non-image capture device 150, processing appliance 148, and client devices 164.

Figure 2:
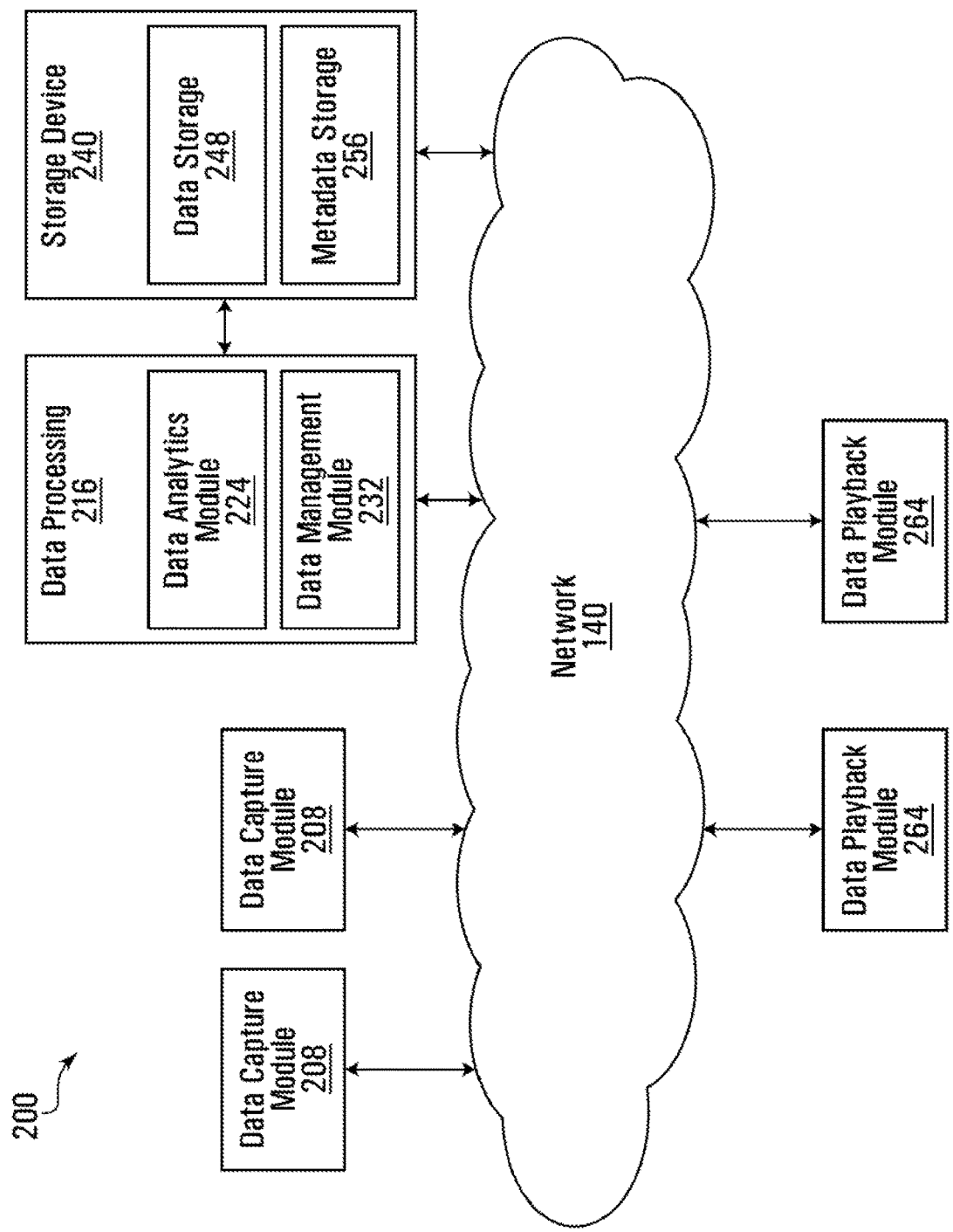
FIG. 2 illustrates a block diagram of a set of operational modules of the data capture and playback system according to the example embodiment of FIG. 1.

Referring now to FIG. 2, there is illustrated a block diagram of a set 200 of operational modules of the data capture and playback system 100 according to one example embodiment. The operational modules may be implemented in hardware, software, or both on one or more of the devices of the data capture and playback system 100 as illustrated in FIG. 1.

The set 200 of operational modules include at least one data capture module 208. For example, each image capture device 108 may implement the data capture module 208 as an image data capture module. The data capture module 208 is operable to control one or more components (such as, for example, sensor 116, etc.) of an image capture device 108 to capture images.

The set 200 of operational modules includes a subset 216 of data processing modules. For example, and as illustrated, the subset 216 of data processing modules includes a data analytics module 224 and a data management module 232.

The data analytics module 224 receives image and non-image data and analyzes that data to determine properties or characteristics of the captured image or video and/or of objects found in the scene represented by the image or video, and of representations in the non-image data such as radar signatures. Based on the determinations made, the data analytics module 224 may further output metadata providing information about the determinations. Examples of determinations made by the data analytics module 224 may include one or more of foreground/background segmentation, object detection, object tracking, object classification, virtual trip-wire, anomaly detection, facial detection, facial recognition, license plate recognition, identification of objects "left behind" or "removed", and business intelligence. However, it will be understood that other analytics functions (video or otherwise) known in the art may also be implemented by the data analytics module 224.

The data management module 232 receives image and non-image data and performs processing functions on that data related to image and non-image data transmission, playback and/or storage. For example, the data management module 232 can process that data to permit its transmission according to bandwidth requirements and/or capacity. The data management module 232 may also process the image data according to playback capabilities of a client device 164 (FIG. 1) that will be playing back video, such as processing power and/or resolution of the display of the client device 164. The data management 232 may also process the image and non-image data according to storage capacity within the data capture and playback system 100 for storing that data.

It will be understood that the subset 216 of data processing modules may, in accordance with some example embodiments, include only one of the data analytics module 224 and the data management module 232. Also, in accordance with other alternative example embodiments, the subset 216 of data processing modules may include more data processing modules than the data analytics module 224 and the data management module 232.

The set 200 of operational modules further include a subset 240 of storage modules. For example, and as illustrated, the subset 240 of storage modules includes a data storage module 248 and a metadata storage module 256. The data storage module 248 stores image and/or non-image data, which may be data processed by the data management module 232. The metadata storage module 256 stores information data outputted from the data analytics module 224.

It will be understood that while the data storage module 248 and metadata storage module 256 are illustrated as separate modules, they may be implemented within a same hardware storage device whereby logical rules are implemented to separate stored image and non-image data from stored metadata. In other example embodiments, the data storage module 248 and/or the metadata storage module 256 may be implemented within a plurality of hardware storage devices in which a distributed storage scheme may be implemented. In at least some example embodiments in which distributed storage is used, some image data, non-image data, and/or metadata may be stored locally to the data capture and playback system 100, and some image data, non-image data, and/or metadata may also be stored on distributed storage remote from the system 100, such as on cloud storage. For example, image data, non-image data, and/or metadata of an entire event may be stored locally on the system 100, and select portions of that image data, non-image data, and/or metadata may be concurrently stored on cloud storage. As another example, image data, non-image data, and/or metadata may be stored, in its entirety, both locally and on cloud storage for backup purposes. As another example, some image data, non-image data, and/or metadata may be stored locally, and additional image data, non-image data, and/or metadata may be stored on cloud storage, with the data stored locally differing from the data stored on cloud storage.

The set of operational modules further includes at least one data playback module 264, which is operable to receive image data, non-image data, and/or metadata derived therefrom and visualize that data and/or metadata. The data playback module 264 may play back video when it receives image data, and may also be used to visualize non-image data. For example, non-image data in the form of radar signatures may be used to generate metadata in the form of a depth map that changes over time, and the data playback module 264 may be used to display an animated depth map. As another example, the non-image data may comprise readings from 6DOF sensor, and acceleration readings from that sensor may be visualized as graphs of acceleration over time and displayed using the data playback module 264. The data playback module 264 may be implemented on a client device 164.

The operational modules of the set 200 may be implemented on one or more of the image capture device 108, non-image capture device 150, processing appliance 148, workstation 156, and client device 164 shown in FIG. 1. In some example embodiments, an operational module may be wholly implemented on a single device. For example, the data analytics module 224 may be wholly implemented on the workstation 156. Similarly, the data management module 232 may be wholly implemented on the workstation 156.

In other example embodiments, some functionalities of an operational module of the set 200 may be partly implemented on a first device while other functionalities of an operational module may be implemented on a second device. For example, data analytics functionalities may be split between one or more of an image capture device 108, non-image capture device 150, processing appliance 148, and workstation 156. Similarly, data management functionalities may be split between one or more of an image capture device 108, non-image capture device 150, processing appliance 148, and workstation 156.

Figure 3:
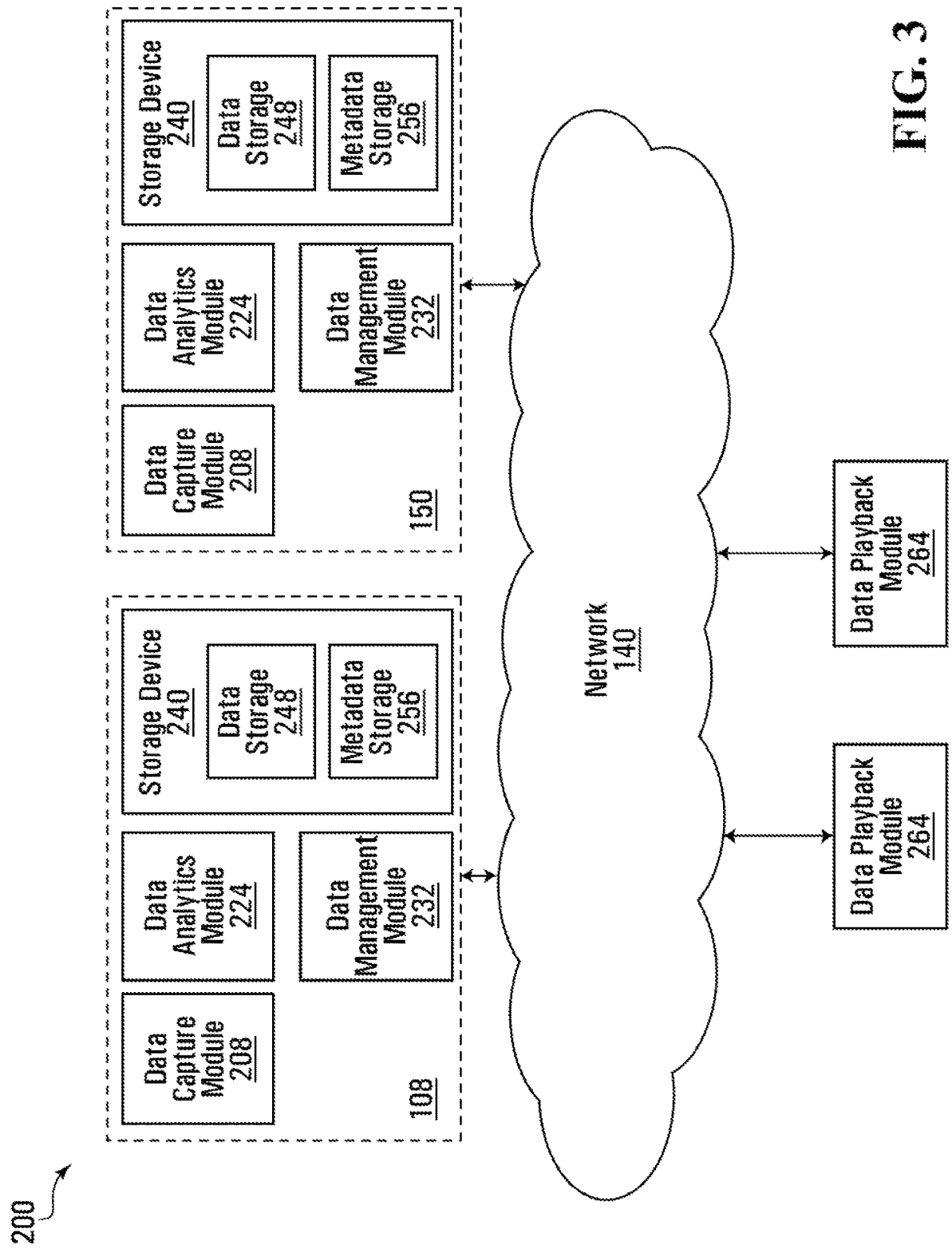
FIG. 3 illustrates a block diagram of a set of operational modules of the data capture and playback system according to the example embodiment of FIG. 1 in which a data capture module, data analytics module, a data management module, and a storage device are wholly implemented on one or more data capture devices included in the data capture and playback system.

Referring now to FIG. 3, there is illustrated a block diagram of a set 200 of operational modules of the data capture and playback system 100 according to one particular example embodiment wherein the data analytics module 224, the data management module 232, and the storage device 240 are wholly implemented on the one or more image capture devices 108 and non-image capture devices 150. Alternatively, the data analytics module 224, the data management module 232, and the storage device 240 are wholly implemented on the processing appliance 148.

It will be appreciated that allowing the subset 216 of data processing modules to be implemented on a single device or on various devices of the data capture and playback system 100 allows flexibility in building the system 100.

For example, one may choose to use a particular device having certain functionalities with another device lacking those functionalities. This may be useful when integrating devices from different parties (e.g. manufacturers) or retrofitting an existing data capture and playback system.

In certain scenarios, it may be useful to be able to monitor an object-of-interest in a region, particularly when the region is sufficiently large that it is monitored by multiple image capture devices 108 and non-image capture devices 150. The monitoring may take any one of multiple forms. For example, in at least some example embodiments the region being monitored may comprise multiple rooms that are concurrently monitored by multiple non-image capture devices 150 in the form of position detectors, such as radar sensors, and multiple image capture devices 108, such as RGB cameras. As objects-of-interest in the form of persons pass through the rooms, they may be monitored by at least one of the non-image capture devices 150 and at least one of the image capture devices 108. The image data and non-image data may be correlated, with the correlation resulting in a determination of which objects-of-interest identified in the non-image data correspond to which objects-of-interest depicted in the image data. A tracking indicator can then be displayed, indicating that correspondence, and permitting a user to track the objects-of-interest.

In at least some of the depicted example embodiments discussed below, at least portions of the region are concurrently monitored by the image capture devices 108 and non-image capture devices 150; however, in at least some other example embodiments, the region may not be concurrently monitored in this way. For example, certain portions of the region may be monitored only by the image capture devices 108 while other portions may be monitored only by the non-image capture devices 150. Additionally or alternatively, one portion of the region may be monitored by the image capture 108 devices at one time, and by the non-image capture devices 150 at another time.

In at least some example embodiments herein, the data collected by various sensors may be spatially and/or temporally correlated and used to construct a database that stores an annotated journey, or trajectory, for each object-of-interest being monitored. For example, when the object-of-interest is a person, at any given point on that person's journey the database may store for that person an appearance clip, face clip, body temperature, breathing rate, and/or cell phone RF signature. The database can be used to support complex search features, as discussed further below.

Figure 5:
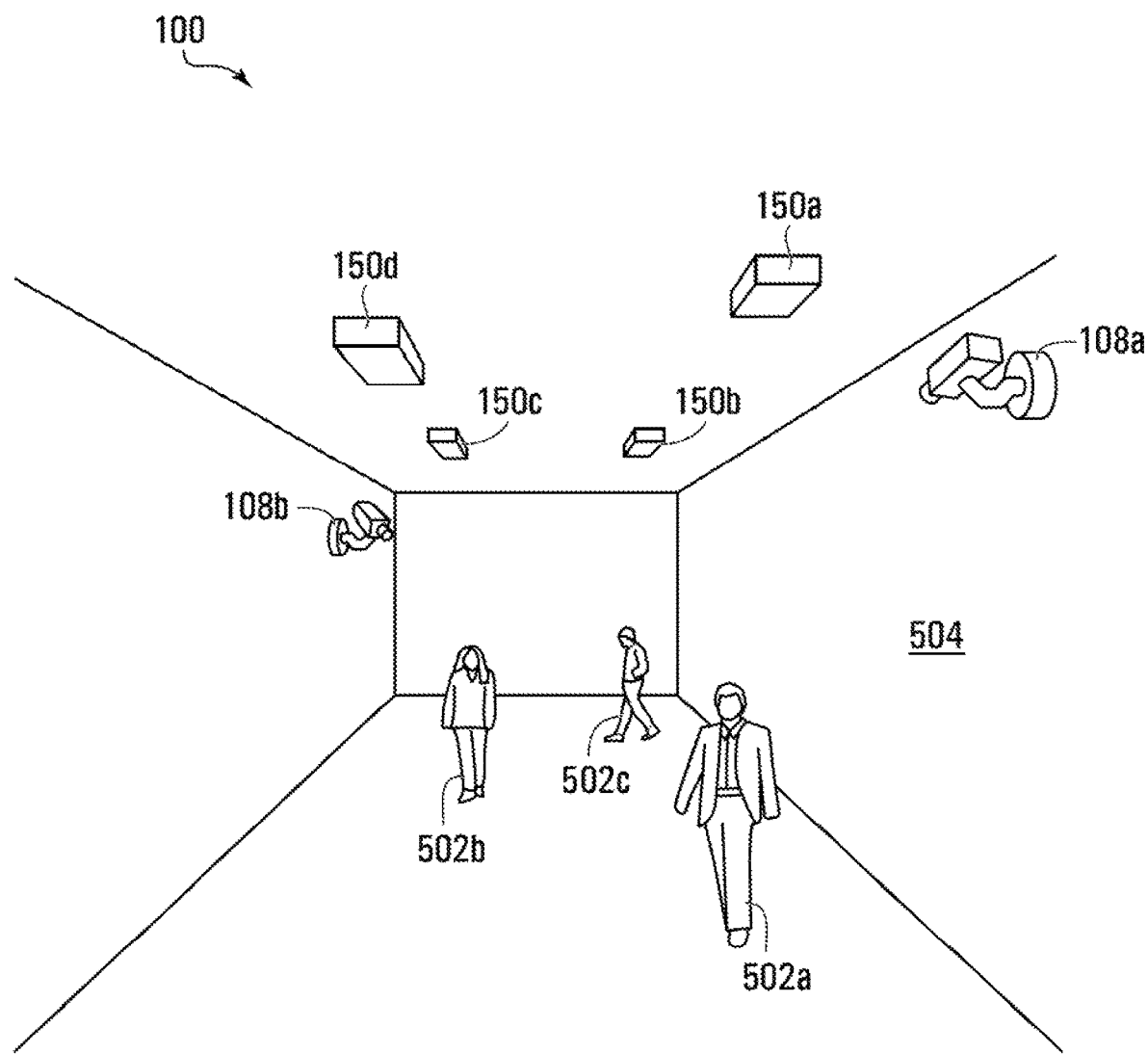
FIG. 5 depicts a system for monitoring an object-of-interest in a region, according to one example embodiment.

Referring now to FIG. 5, there is depicted a system 100 for monitoring an object-of-interest in a region, according to one example. The system 100 is installed in a room 504 and comprises first through fourth non-image capture devices 150a-d installed on the room's 504 ceiling. In at least the example embodiment of FIG. 5, each of the devices 150a-d comprises a non-image sensor 152 in the form of a radar sensor, and the devices 150a-d are accordingly "active devices" in that they emit a radar signal and measure the resulting reflected radar signal. In at least some different embodiments, any one or more of the non-image capture devices 150a-d may alternatively be passive devices (e.g., devices that do not emit a signal for reflection into the region being monitored), or be a different type of active device (e.g., the device 150 may monitor by emitting and measuring mmWave signals).

Each of the devices 150a-d is positioned to generate non-image data by scanning approximately one-quarter of the room 504. Mounted on opposing walls and at different ends of the room 504 are first and second image capture devices 108a,b in the form of RGB cameras configured to capture image data in the form of RGB images. In the example embodiment of FIG. 5, the devices 108a,b, 150a-d monitor first through third objects-of-interest 502a-c. While in the depicted embodiment the devices 150a-d are installed on the room's 504 ceiling, in different embodiments (not depicted) any one or more of them may be installed at a different location. For example, when monitoring the room 504, any one or more of the devices 150a-d may be wall-mounted, installed in the floor, or worn by one of the objects-of-interest 502a-c. The mounting location of one or both of the image capture devices 108a,b may similarly be varied.

Figure 4A:
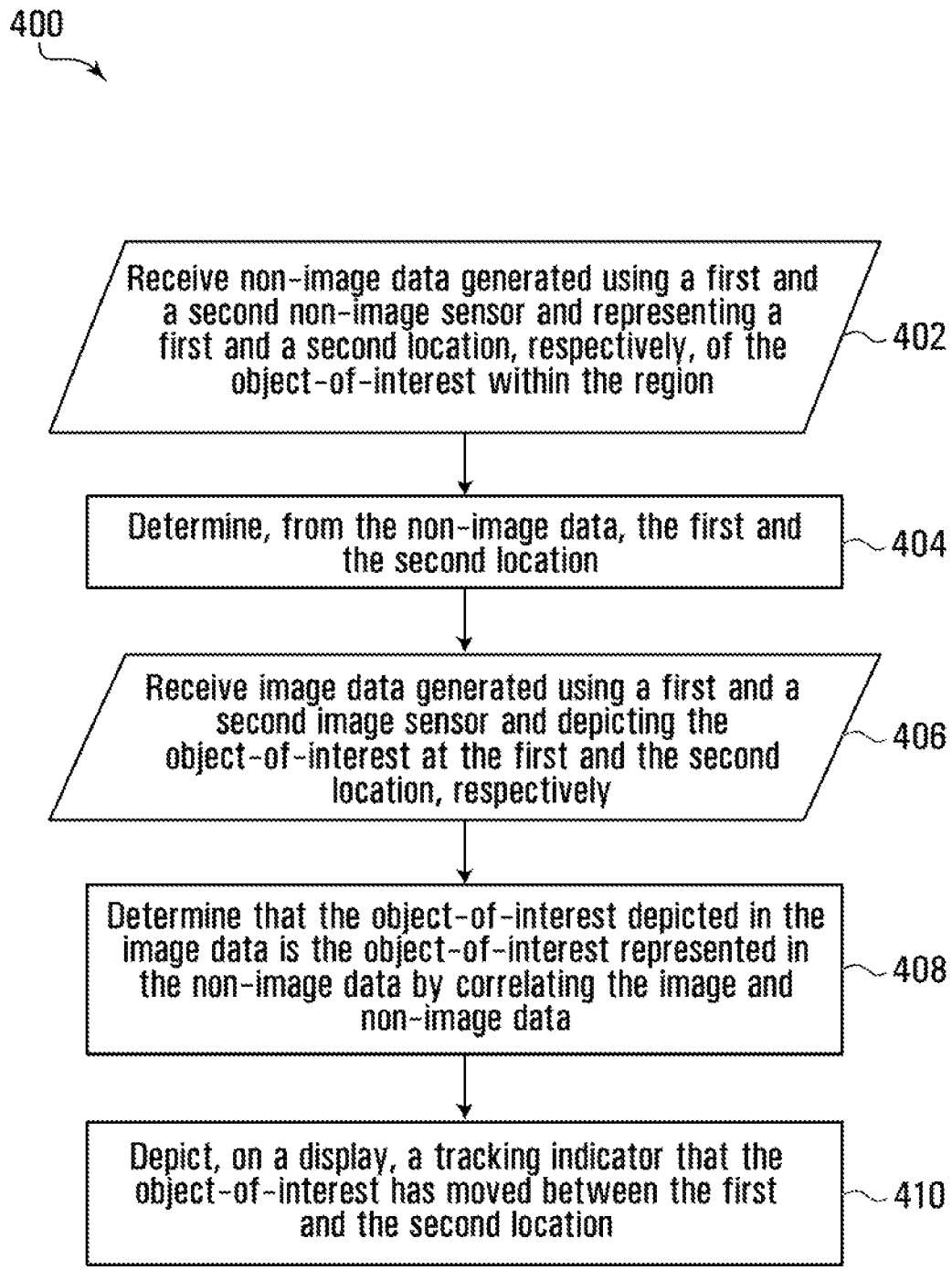
FIGS. 4A and 4B depict methods for monitoring an object-of-interest in a region, according to additional example embodiments.

Referring now to FIG. 4A, there is shown an example embodiment of a method 400 for monitoring an object-of-interest 502 within a region. When applied in the example context of FIG. 5, the method 400 may be performed by the data analytics module 224. The module 224 receives non-image data generated using a first and a second non-image sensor 152 and representing a first and a second location, respectively, of the object-of-interest 502 (block 402) within the region. Those skilled in the art will recognize the existence of different manners in which the data analytics module 224 is able to register that an object in the first location is the same object as in the second location. For example, appropriate system calibration can be employed to correlate data from each respective source within a common coordinate system, system learning can be employed to generate associations with respect to objects moving within a scene, etc. The module 224 determines, from the non-image data, the first and the second location (block 404). In an example embodiment in which each of the non-image sensors 152 comprises a radar sensor, the non-image data may be used to determine the location of the object-of-interest 502; doing this may comprise generating a depth map using non-image data collected using the radar sensor. For example, the radar data collected is processed and used to determine metadata representing the location of the object-of-interest 502; alternatively, the non-image capture device 150 may directly output data representing the object-of-interest's location 502. The module 224 also receives image data generated using a first and a second image sensor 116 and depicting the object-of-interest at the first and the second location, respectively (block 406). Once the module 224 has the image and the non-image data, it determines that the object-of-interest 502 depicted in the image data is the object-of-interest 502 represented in the non-image data by correlating the image and the non-image data (block 408).

The correlation may be done in any one or more of a variety of ways. In at least some example embodiments in which the non-image data and image data are not substantially spatially correlated, such as when the non-image data is generated using radar signals, feature or pixel level correlation may be performed on the image and non-image data. Take as an example radar data and visible light image data. These may not have the same resolution, so perhaps only one blob appears in the radar data (or say two blobs, one for head and one for body). This coarse feature detection of body, head and/or limb can be correlated to a group of pixels in the visible light image. In at least some example embodiments in which the non-image data and image data are substantially spatially correlated, a convolutional neural network may be used to perform correlation. Feature or pixel level correlation can also be performed when the image and non-image data are substantially spatially correlated (i.e. as can be done when the data are not substantially spatially correlated, and a convolution neural network can be employed here as well). In at least some example embodiments, each of the image and non-image data are time-stamped (and noting that all portions of a same image will have the same timestamp) and correlation comprises associating those portions of the non-image and image data having a common timestamp with each other. Combining different types of data together may be done using spatial analytics, for example, and/or other methods that enable associations to be formed between data and/or metadata resulting from measurements collected using different sensors.

After correlating at block 408, the module 224 depicts, on a display, a tracking indicator indicating that the object-of-interest 502 has moved between the first and the second location (block 410).

In at least some of the example embodiments discussed herein, the system 100 may also obtain non-image metadata associated with the non-image data and image metadata associated with the image data. The position metadata referred to in the above example embodiments may comprise part of the non-image metadata. The image metadata may comprise appearance data for the object-of-interest; an example of that appearance data comprises, in at least some example embodiments, metadata directed at foreground/background segmentation, object detection (e.g., bounding boxes), object tracking, and object classification, as discussed above. Following determining that the object-of-interest 502 depicted in the image data is the object-of-interest 502 identified in the non-image data at block 408 of FIG. 4A, the system 100 may associate the non-image metadata and the image metadata together and use the combined, or "fused", metadata to implement the example embodiments herein. The system 100 stores metadata that has been "fused" or combined in this manner is stored in the metadata storage module 256.

Figure 6A:
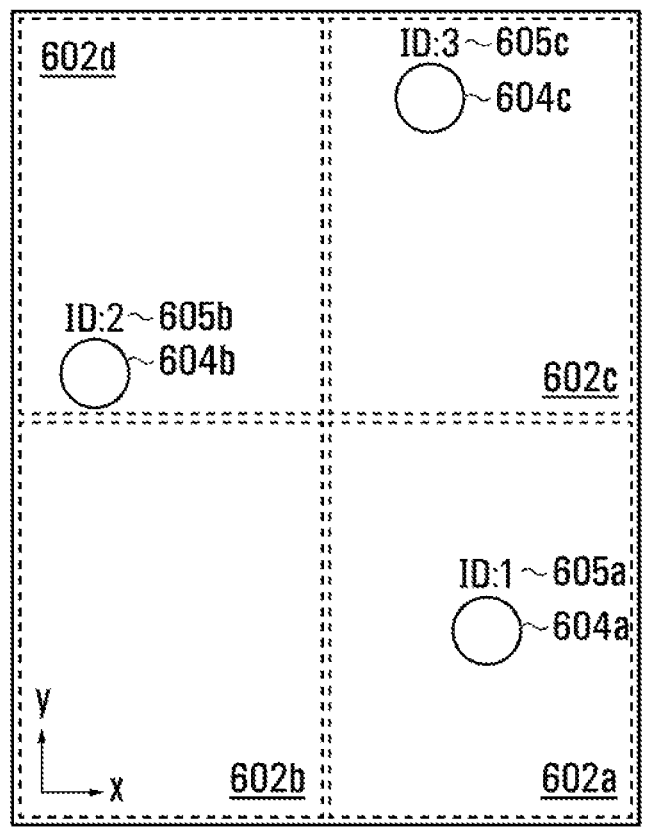
FIGS. 6A and 6B depict screenshots of a user interface showing objects-of-interest as captured using non-image capture devices (FIG. 6A) and cameras (FIG. 6B), in which the non-image data used to generate FIG. 6A and the image data used to generate FIG. 6B have been correlated with each other.
Figure 6B:
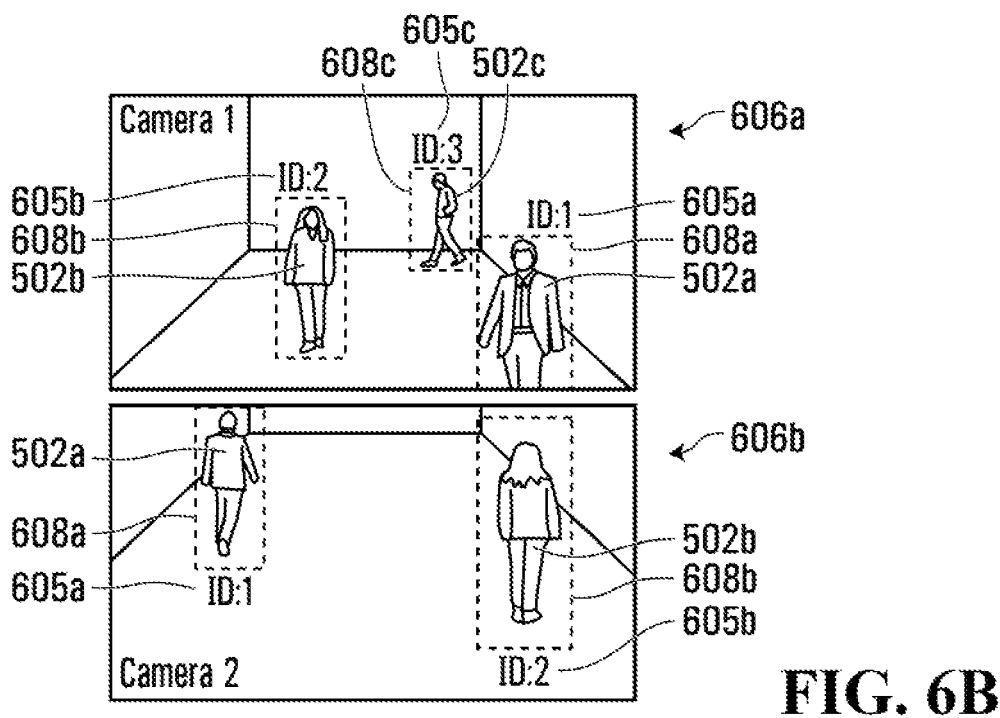

Referring now to FIGS. 6A and 6B, there are depicted screenshots of a user interface showing the objects-of-interest 502a-c as captured using the non-image capture devices 150a-d (FIG. 6A) and the image capture devices 108a,b (FIG. 6B), in which the non-image data and the image data have been correlated with each other. In FIG. 6A, the room 504 has been divided into first through fourth scanning regions 602a-d, which are scanned by the first through fourth non-image capture devices 150a-d, respectively. A first object-of-interest indicator 604a representing the location of the first object-of-interest 502a is depicted in the first scanning region 602a; a second object-of-interest indicator 604b representing the location of the second object-of-interest 502b is depicted in the fourth scanning region 602d; and a third object-of-interest indicator 604c representing the location of the third object-of-interest 502c is depicted in the third scanning region 602c. In FIG. 6B, the room 504 is viewed from two perspectives: a first field-of-view 606a representing the perspective captured by the first image capture device 108a, and a second field-of-view 606b representing the perspective captured by the second image capture device 108b. The first field-of-view 606a shows the first through third objects-of-interest 502a-c around which are first through third bounding boxes 608a-c, respectively. The second field-of-view 606b shows the first and second objects-of-interest 502a,b around which are the first and second bounding boxes 608a,b, respectively.

Above each of the bounding boxes 608a-c in the fields-of-view 606a,b and the object-of-interest indicators 604a-c in the scanning regions 602a-d is a correlation indicator; more specifically, first through third correlation indicators 605a-c are shown above the first through third object-of-interest indicators 604a-c and the first through third bounding boxes 608a-c, respectively. In the depicted example embodiment, the first correlation indicator 605a is "ID: 1", the second correlation indicator 605b is "ID: 2", and the third correlation indicator 605c is "ID: 3". The correlation indicators 605a-c are generated using the results of the correlation performed at block 408 of the method 400, and show that the bounding boxes 608a-c and indicators 605a-c having a common correlation indicator 605a-c refer to the same object-of-interest 502a-c. Prior to the correlation being performed at block 408, each of the image capture devices 108a,b and non-image capture devices 150a-d assigns a sensor-unique object identifier to each object-of-interest 502a-c. As a result of the correlation at block 408, the object identifiers are mapped to each other and the system 100 determines which of those object identifiers correspond to which object-of-interest 502a-c, and consequently determines and displays the object-of-interest indicators 605a-c.

While in the depicted example embodiment the correlation indicators 605a-c are text, in at least some different example embodiments (not depicted) the correlation indicators 605a-c may be different. For example, the indicators 605a-c may be graphical (e.g., different colors may be used to represent different objects-of-interest 502a-c), or comprise a combination of text and graphics. In at least some example embodiments, the system 100 for any one of the objects-of-interest 502 displays a tracking indicator by showing the first and second fields-of-view 606a, b, the bounding box 608 for that object-of-interest 502, and the correlation indicator 605 for that object-of-interest 502 as that object-of-interest moves from the first location in the first field-of-view 606a to the second location in the second field-of-view 606b, thereby allowing the user to track the object-of-interest 502 as it moves within the region.

Figure 7A:
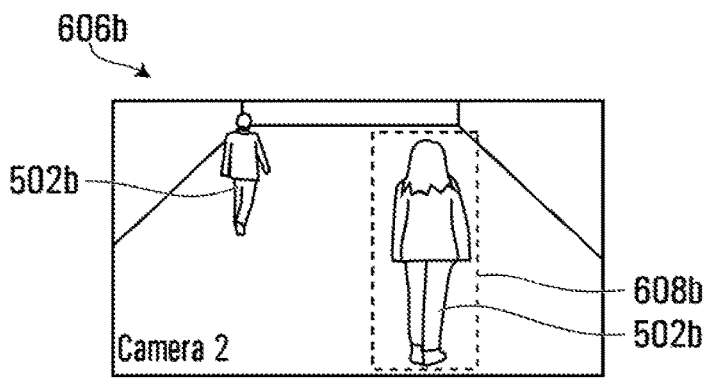
FIGS. 7A-7E depict screenshots of a user interface showing an object-of-interest being monitored in a region using a combination of image data and non-image data, according to one example embodiment.
Figure 7B:
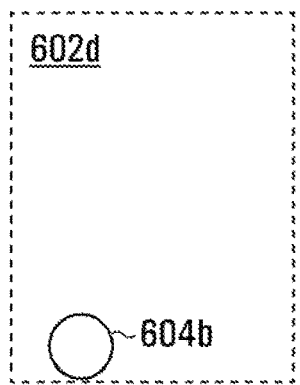

Referring now to FIGS. 7A-7E, there are depicted screenshots of a user interface showing an object-of-interest 502b being monitored in a region using a combination of image data and non-image data using the system 100 of FIG. 5, according to another example embodiment. FIG. 7A depicts the second field-of-view 606b as captured by the second image capture device 108b. Within the second field-of-view 606b are the first and second objects-of-interest 502a,b, with the second object-of-interest 502b being surrounded by the second bounding box 608b. FIG. 7B depicts the fourth scanning region 602d, which corresponds to the location of the second object-of-interest 608b as shown in the second field-of-view 606b. Accordingly, the second object-of-interest indicator 604b is depicted within the fourth scanning region 602d.

Figure 7C:
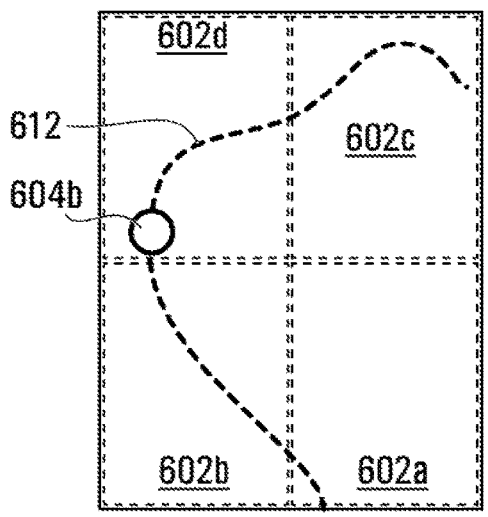

As the object-of-interest 502b moves through the region, she is monitored by the image capture devices 108a,b and the non-image capture devices 150a-d. FIG. 7C depicts all four of the scanning regions 602a-d as well as a tracking indicator in the form of a path indicator 612 depicting a trajectory traveled by the object-of-interest 502b as she moves through the region over time.

Figure 7D:
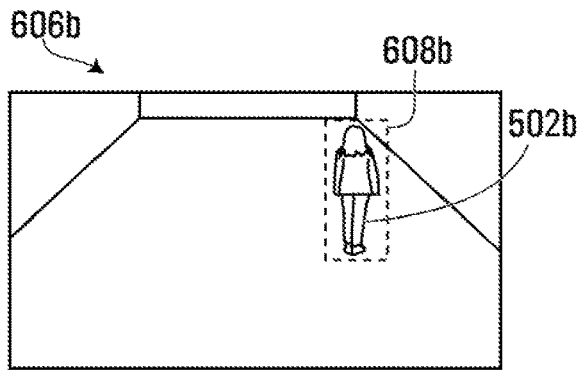
Figure 7E:
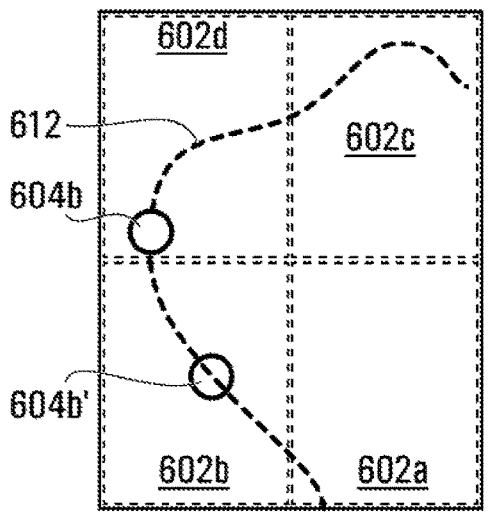

Referring now to FIG. 7E, there is depicted the object-of-interest indicator 604b at two locations: a first location, which is the location at which the object-of-interest indicator 604b is also depicted in FIG. 7C and which corresponds to the location of the object-of-interest 502b in FIG. 7A; and a second location, which is the location at which the object-of-interest indicator is depicted in FIG. 7E using label 604b', and which corresponds to the location of the object-of-interest 502b in FIG. 7D. As FIG. 7E shows, the path indicator 612 intersects the first and second locations.

In at least some example embodiments, a user may provide input to the system 100 that the object-of-interest 604b indicator is to move to from the first location to the second location. This input may comprise selecting, using an input device such as a mouse or touchscreen, the portion of the path indicator 612 that corresponds to the second location. In response to this input, the system 100 displays the object-of-interest indicator 604b' at the second location, the field-of-view 606b depicting the object-of-interest 502b at the second location, and a bounding box 608b around the object-of-interest 502b; an example of such a display is in FIG. 7D. The system 100 may display both FIGS. 7D and 7E concurrently, allowing the user to more easily visually correlate where the object-of-interest 502b is using both image and non-image data; alternatively, the system 100 may display only one of FIGS. 7D and 7E at any given time and allow the user to swap between the two. In FIGS. 7D and 7E, as there is only a single object-of-interest 502b, there is no explicit correlation indicator 605 akin to that shown in FIGS. 6A and 6B. In at least some different example embodiments, the correlation indicator 605 may be shown notwithstanding there being only a single object-of-interest 502b depicted. Additionally, in at least some example embodiments when many objects are depicted in a region but there is only one object-of-interest 502 being tracked, the one object-of-interest 502 being tracked may be the only object identified using a bounding box 608 and object-of-interest indicator 604, thereby implying correlation.

The workflow described in respect of FIGS. 7A-7E above may commence in response to the system's 100 receiving a signal to commence a search for the object-of-interest 502b.

For example, a user may provide a user input that evokes a context menu, and from that context menu commence a search for the object-of-interest 502b.

As discussed above, the system 100 stores the image and non-image data it collects in the data storage module 248, and all image metadata and non-image metadata in the metadata storage module 256. The stored metadata comprises the combined or "fused" metadata. The image and non-image data are correlated with each other, and through this correlation, image clips of the object-of-interest 502 can be automatically associated with the location of that object-of-interest 502 that is scanned using the non-image data sensors 152. This allows the system 100 to maintain in the storage device 240 or another database (not shown) all location/motion information and surveillance footage for one or more objects-of-interest 502 in a monitored region. For example, in at least some example embodiments, fusing cross-sensor object tracking metadata allows the system 100 to form more complete object trajectories, and to associate those trajectories with that object's appearance. This enables a use case for a forensic timeline view of an object's complete journey within a monitored region. For example, when the objects being monitored are persons, associating captured faces with a person's recorded journey enables a similar appearance search within and across multiple visits to and trips through the region.

Similarly, associating information captured by Bluetooth™ or Wi-Fi™ RF sensors 152 with a person's journey helps connect appearances across different sensors 116,152, and also potentially across visits to the region.

The system 100 can accordingly collect and construct graph-like associations between metadata information from many sensors 116,152 to construct an approximate description of a physical environment referred to as a "world model".

The world model may be based on sensor data describing the foreground objects present and moving within an environment, but may also additionally or alternatively comprise static objects the system 100 detects in the background, either by image classification (e.g., cash register, parking meter, ATM, etc.), or statistically (e.g., features like doorways).

Behavioral metadata can also be produced by new video analytics, by statistically processing video analytic metadata (classified objects), or by deep learning methods (gesture detection/recognition). This is metadata describing the behavior of individual foreground objects and the interactions foreground objects have with one another, and with background objects.

Using the world model stored in the database, users of the system 100 may search the storage device 240 for behaviors of interest in real-time or after they have occurred, and may actively monitor for and set alarms to behaviors of potential interest as they occur. Examples of behaviors that the system 100 may be trained to search for comprise the following:
 a. loitering, by combining image data and 3D and/or radar sensor data, to prevent a still person from being mistaken for background;
 b. a person gesturing for assistance in a retail venue;
 c. a person gesturing in a manner that represents spray-painting or another form of vandalism;
 d. a person demonstrating an atypical trajectory, such as a trajectory used to avoid an obstacle, circle an object, or that abnormally corresponds or relates to a trajectory of another object (e.g., as may result from one person fleeing or chasing the other);
 e. a person appearing or disappearing within a certain spatial and temporal proximity of a vehicle, which may represent that person exiting or entering that vehicle;
 f. a sudden and/or significant change to a person's face or appearance;
 g. a person taking actions that span multiple image and/or non-image capture devices 108,150 (e.g., a person entering a doorway after exiting a vehicle and then proceeding directly to an airport security checkpoint without first checking in any baggage);
 h. a person loitering within a region and, while loitering, being proximate to and appearing to interact with other persons, which may represent illicit activities being conducted; and
 i. a person demonstrating aggressive behavior to another person.

It will be understood that, depending on the scenario, certain non-image data may complement potential weaknesses of image data associated with traditional video. For example, loitering 3D or radar sensor data can help to track a person and prevent/mitigate the person being confused as background. For gesturing or person trajectory, a different angle data may help with problems due to occlusion. For spray painting, radar may potentially augment detection of a metal can and may result in a stronger confidence in that behavior when detected.

Figure 8A:
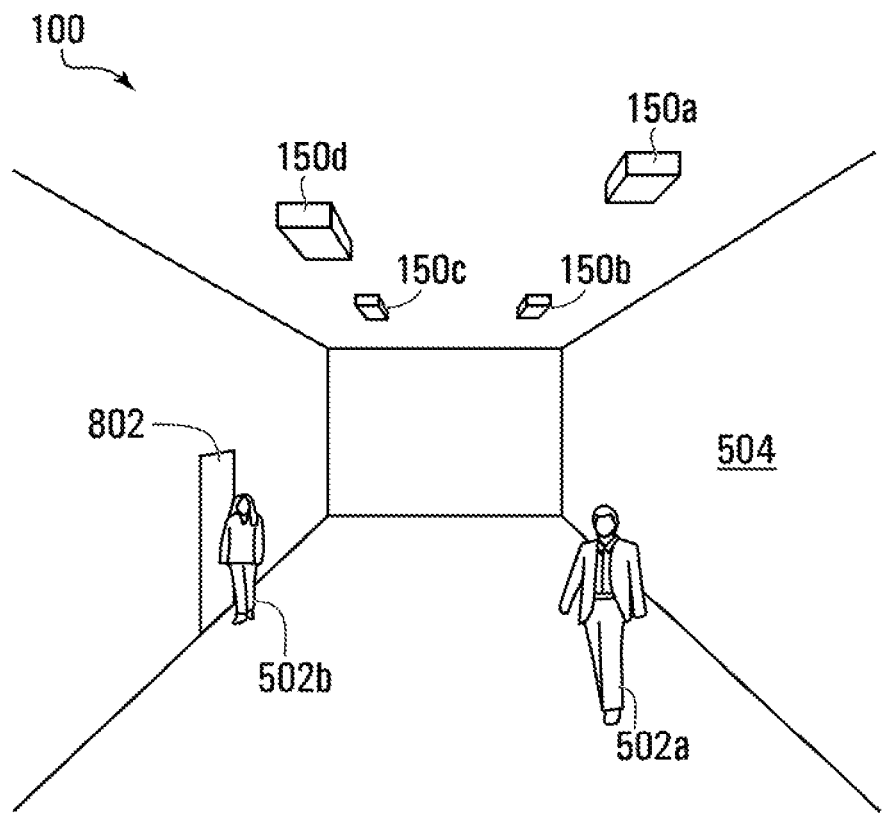
FIG. 8A depicts a system for monitoring an object-of-interest in a region, according to one example embodiment.

Referring now to FIG. 8A, there is depicted the system 100 for monitoring an object-of-interest 502 in a region, according to an example embodiment in which the region is a room 504 having a doorway and the system 100 is configured to monitor persons entering or leaving the room 504. The room 504 of FIG. 8A is identical to the room 504 of FIG. 5, with the exception that the room 504 of FIG. 8A comprises a doorway 802 through which objects-of-interest 502 may enter and exit.

Figure 8B:
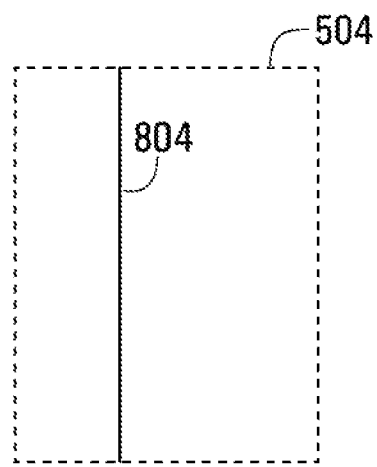
FIG. 8B depicts a threshold distance used to determine when a person has entered or has left a room in which the system of FIG. 8A has been installed.

The system 100 of FIG. 8A is configured to detect when an object-of-interest 502 crosses past a threshold distance from the doorway 802, as depicted in FIG. 8B. FIG. 8B shows a line 804 that is parallel to a wall of the room 504 in which the doorway 802 is located, and the threshold distance is the length of another line (not shown) that extends between and is normal to both of that wall and the line 804. In at least some different example embodiments (not depicted), the threshold distance may be differently defined; for example, the threshold distance may be a constant distance from the center of the doorway 802, in which case it would be represented in FIG. 8B as a semi-circle centered on the doorway 802.

The system 100 in at least some example embodiments keeps a count of a number of persons in the room 504 based on persons' positions relative to the threshold distance. More particularly, the system 100 uses position metadata obtained using the position detectors that comprise the non-image capture devices 150a-d to determine whether an object-of-interest 502 in the form of a person has crossed past the threshold distance following entering the room 502; if yes, the system 100 increments the count of the number of persons in the room by one. Analogously, the system 100 also uses the position metadata to determine whether a person has transitioned from, relative to the doorway 802, being outside of the threshold distance to within the threshold distance. When the person has so transitioned, the system 100 decreases the count of the number of persons in the room 504.

Figure 9:
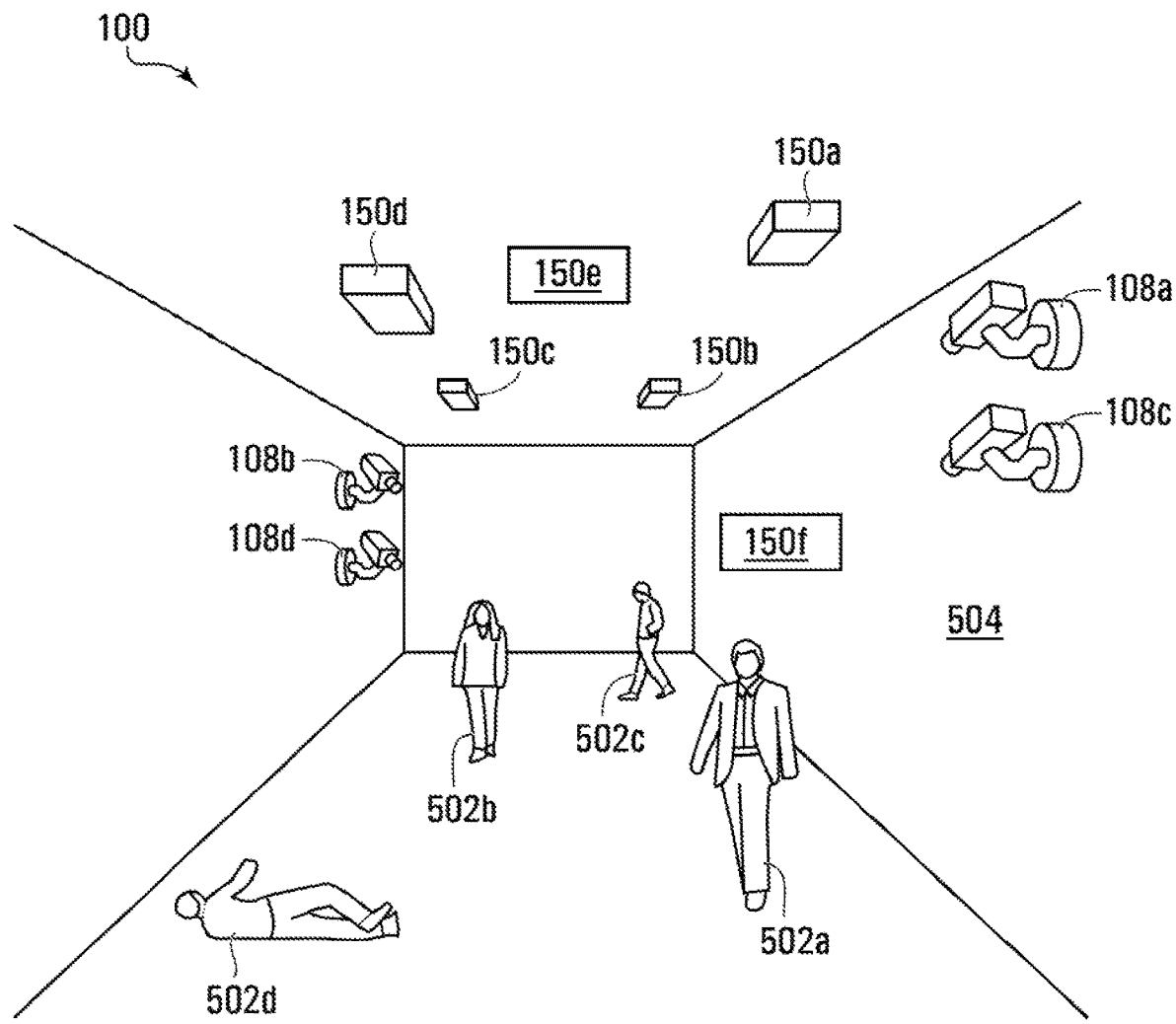
FIG. 9 depicts a system for monitoring an object-of-interest in a region, according to one example embodiment.

FIG. 9 depicts another example embodiment of the system 100 that may be deployed in a hospital or other caregiving environment. The system 100 of FIG. 9 monitors first through fourth objects-of-interest 502a-d in the form of persons who are seeking medical attention. As with the system 100 of FIG. 5, the system 100 of FIG. 9 comprises the first and second image capture devices 108a,b positioned at opposing ends of the room to capture the first and second fields-of-view 606a,b. The system 100 of FIG. 9 also comprises third and fourth video captures devices 108c,d in the form of thermal cameras positioned below the first and second image capture devices 108a,b, respectively, such that their respective fields-of-view are substantially spatially correlated.

The system 100 of FIG. 9 also comprises the first through fourth non-image capture devices 150a-d mounted on the ceiling and positioned to collectively scan the entire room 502. The first through fourth devices 150a-d of FIG. 9 are 3D cameras, which are used to determine persons' locations within the 3D cameras' fields of view. The system 100 of FIG. 9 also comprises fifth and sixth non-image capture devices 150e,f: the fifth device 150e comprises a radar sensor positioned on the ceiling and the sixth device 150f comprises an RF sensor positioned on a wall.

In FIG. 9, the RF sensor is configured to detect RF signals, such as Bluetooth™ and Wi-Fi™ signals, emanating from the objects-of-interests' 502a-d mobile phones and other devices. The radar sensor is a position detector that can be used to track the objects-of-interests' 502a-d vital signs, such as rate-of-respiration and heart rate. The 3D cameras are used for positioning information, and can be combined with the image data obtained from the image capture devices 108a,b to assist in object segmentation. One or both of the 3D cameras and radar sensor can also assist with background adaptation rejection; that is, preventing objects from becoming part of a 2D background.

Figure 10A:
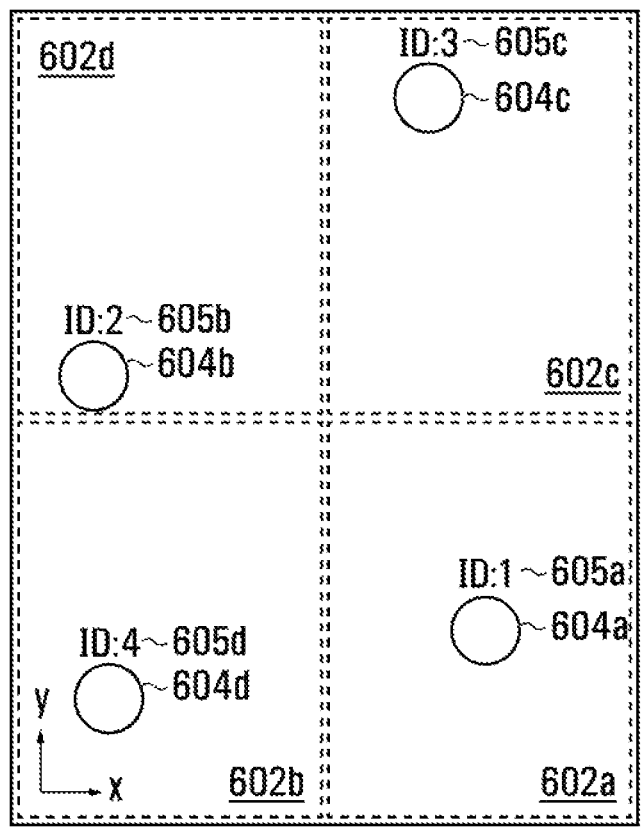
FIGS. 10A-10C depict screenshots of a user interface showing persons being monitored in a region using a combination of image data and non-image data, in which non-image data is used to determine temperature and rate-of-respiration of the persons.
Figure 10B:
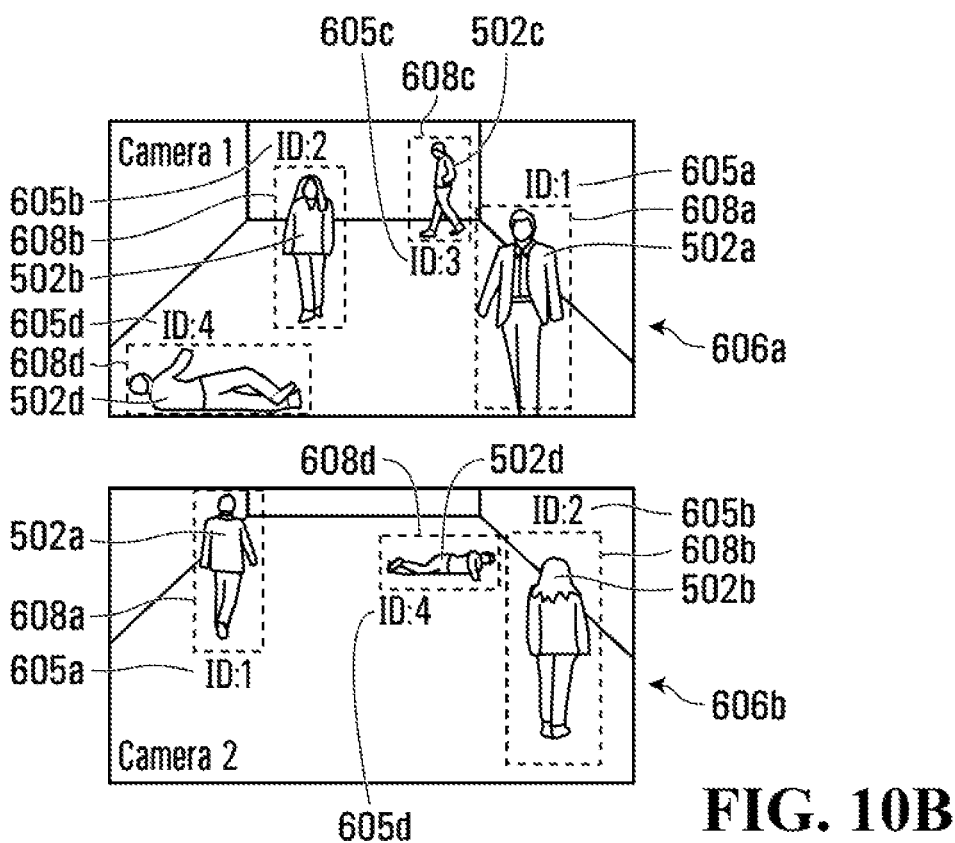

FIGS. 10A and 10B depict screenshots of a user interface showing the objects-of-interest 502a-d as captured using the first through fourth non-image capture devices 150a-d (FIG. 10A) and the image capture devices 108a,b (FIG. 10B). In FIG. 10A, the room 504 has been divided into the first through fourth scanning regions 602a-d, which are scanned by the first through fourth non-image capture devices 150a-d, respectively, and the RF sensor 152, to track the location of the objects-of-interest 502a-d. The first object-of-interest indicator 604a representing the location of the first object-of-interest 502a is depicted in the first scanning region 602a; the second object-of-interest indicator 602b is depicted in the fourth scanning region 602d; the third object-of-interest indicator 604c is depicted in the third scanning region 602c; and the fourth object-of-interest indicator 604d is depicted in the second scanning region 602b. In FIG. 10B, the room 504 is viewed from two perspectives: the first field-of-view 606a representing the perspective captured by the first image capture device 108a, and the second field-of-view 606b representing the perspective captured by the second image capture device 108b. The first field-of-view 606a shows all four of the objects-of-interest 502a-d around which are first through fourth bounding boxes 608a-d, respectively. The second field-of-view 606b shows the first, second, and fourth objects-of-interest 502a,b,d around which are the first, second, and fourth bounding boxes 608a,b,d respectively.

Above each of the bounding boxes 608a-d in the fields-of-view 606a,b and the object-of-interest indicators 604a-d in the scanning regions 602a-d is a correlation indicator; more specifically, first through fourth correlation indicators 605a-d are shown above the first through fourth object-of-interest indicators 604a-d and the first through fourth bounding boxes 608a-d, respectively. In the depicted example embodiment, the first correlation indicator 605a is "ID: 1"; the second correlation indicator 605b is "ID: 2"; the third correlation indicator 605c is "ID: 3"; and the fourth correlation indicator 605d is "ID: 4". The correlation indicators 605a-d are generated using the results of the correlation performed at block 408 of the method 400, and show that the bounding boxes 608a-d and indicators 605a-d having a common correlation indicator 605a-d refer to the same object-of-interest 502a-d. While in the depicted example embodiment the correlation indicators 605a-d are text, in at least some different example embodiments (not depicted) the correlation indicators 605a-d may be different. For example, the indicators 605a-d may be graphical (e.g., different colors may be used to represent different objects-of-interest 502a-d), or comprise a combination of text and graphics. In at least some example embodiments, the system 100 for any one of the objects-of-interest 502 displays a tracking indicator by showing the first and second fields-of-view 606a,b, the bounding box 608 for that object-of-interest 502, and the correlation indicator 605 for that object-of-interest 502 as that object-of-interest moves from the first location in the first field-of-view 606a to the second location in the second field-of-view 606b, thereby allowing the user to track the object-of-interest 502 as it moves within the region.

Figure 10C:
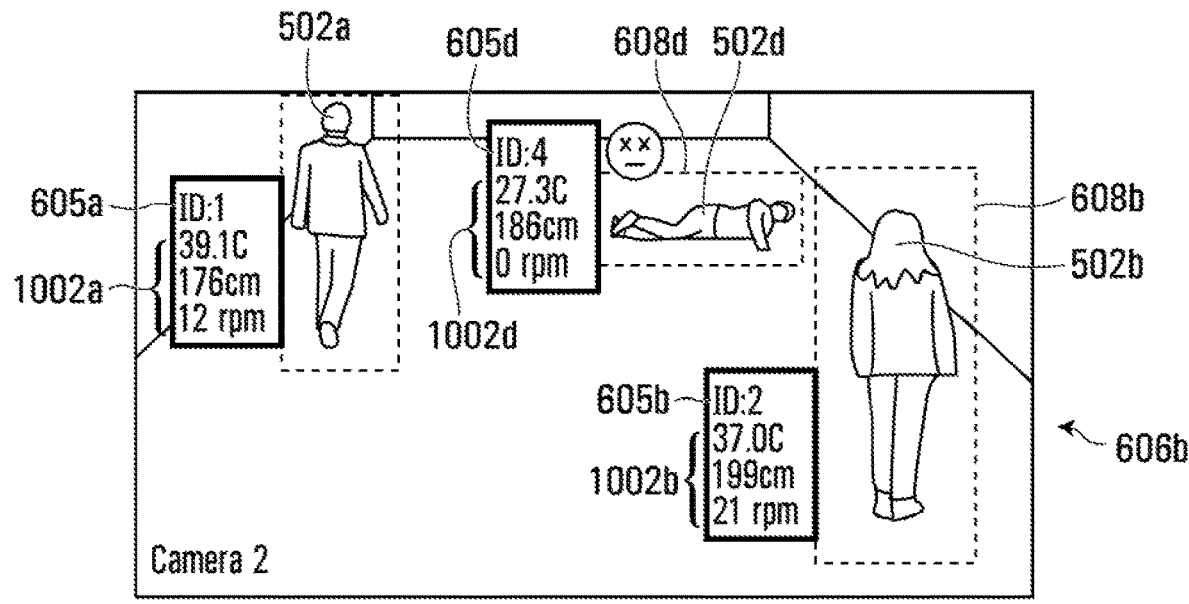

FIG. 10C depicts a screenshot of a user interface in which metadata obtained using the radar sensor and thermal cameras is combined together with the metadata obtained using the rest of the non-image capture devices 150a-e and the image capture devices 108a,b. As a result of the correlation performed at block 408 of FIG. 4, position metadata generated using the raw radar sensor and temperature metadata generated using the thermal cameras is associated with the appropriate objects-of-interest 502a,b,d depicted in FIG. 10C. For each of the objects-of-interest 502a,b,d, the system 100 determines from the position metadata the person's rate-of-respiration and from the thermal data the person's temperature, and this data is displayed in FIG. 10C as biometric metadata 1002a,b,d for the objects-of-interest 502a,b,d, respectively. The biometric metadata 1002a,b,d further comprises a height estimate for each of the objects-of-interest 502a,b,d, which the system 100 determines using data output by the 3D cameras comprising the first through fourth devices 150a-d.

Having access to the biometric metadata 1002a,b,d permits the system 100 to perform biometric monitoring. For example, in at least some example embodiments the system 100 determines for each of the objects-of-interest 502a,b,d whether the rate-of-respiration for that person is below a minimum threshold and, when the rate-of-respiration is below the minimum threshold, the system 100 triggers a rate-of-respiration alarm. Similarly, in at least some example embodiments the system 100 determines for each of the objects-of-interest 502a,b,d whether the temperature for that person is within a temperature range and, when the temperature is outside of that range, the system 100 triggers a temperature alarm. In FIG. 10C, the rate-of-respiration threshold is 10 rpm and the temperature range is from 97.1° F. (36.2° C.) to 99.5° F. (37.5° C.). Accordingly, the system 100 does not trigger the rate-of-respiration or temperature alarms for the second object-of-interest 502b. However, the system 100 does trigger a temperature alarm for the first object-of-interest 502a, who has a temperature of 39.1° C. (102.4° F.), and triggers both the temperature and rate-of-respiration alarms for the fourth object-of-interest 502d.

A system configured in such a manner may be used, for example, to monitor a hospital waiting room to determine whether a patient is unable to further wait for acute care. Elsewhere in a hospital, the system 100 may be deployed to monitor patients in other ways. For example, the system 100 may monitor a patient who is flagged as being unable to safely get out of bed and, if the system 100 detects the patient is attempting to get out of bed unattended, the system 100 may sound an alarm. As another example, a patient may be permitted to roam within a certain room but not permitted to leave that room; in this example, the system 100 may trigger an alarm if the patient leaves that room.

Figure 4B:
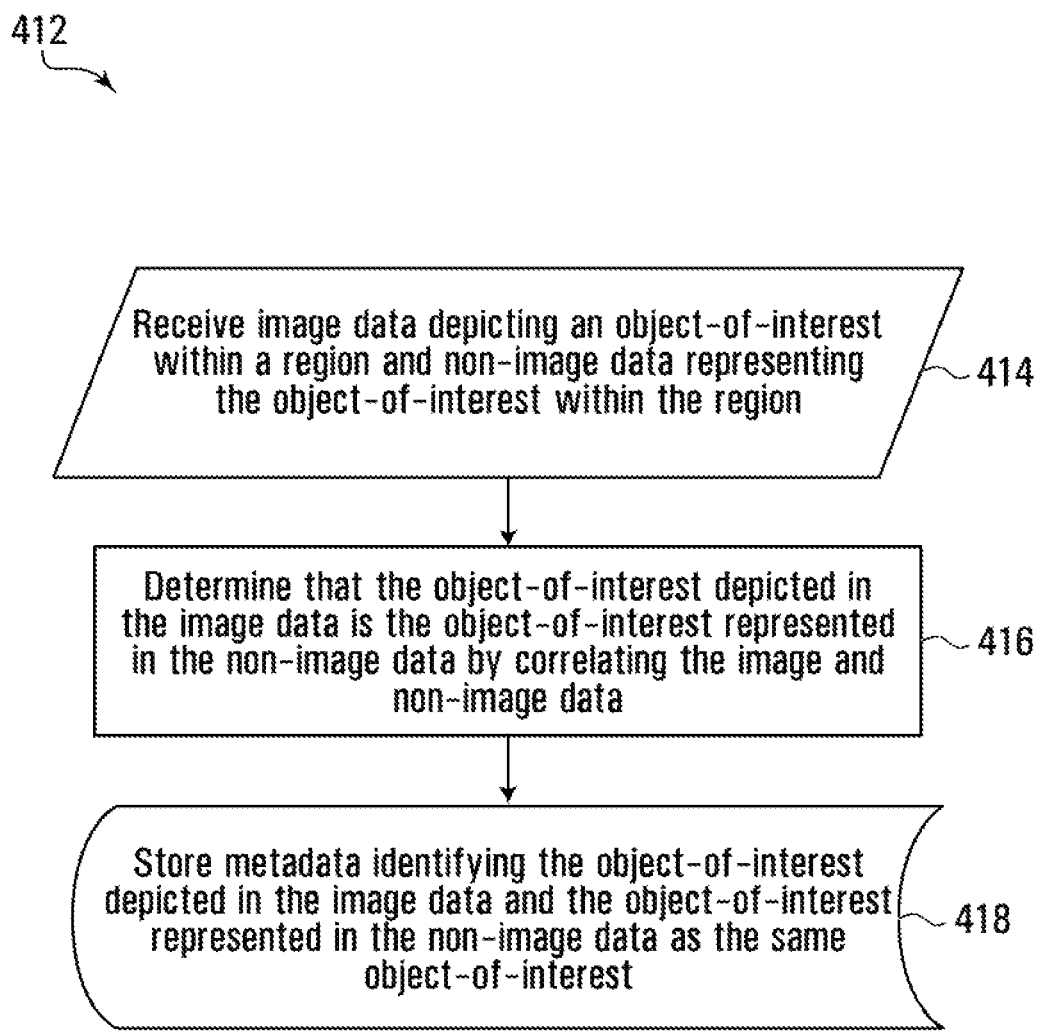

While the example embodiments discussed in FIGS. 4A and 5-10C comprise at least two of the non-image sensors 150 and two of the image sensors 116, more generally at least some example embodiments may comprise a single non-image sensor 150 and a single image sensor 116. FIG. 4B depicts another example embodiment of a method 412 for monitoring an object-of-interest 502 in a region. In the example method 412 of FIG. 4B, the data analytics module 224 at block 414 receives image data depicting an object-of-interest 502 within a region and non-image data representing the object-of-interest 502 within the region. The image and non-image data referred to in block 414 may be collected using one or more non-image capture devices 150 and one or more image capture devices 108. The data analytics module 224 at block 416 determines that the object-of-interest 502 depicted in the image data is the object-of-interest 502 represented in the non-image data by correlating the image and non-image data, as discussed above in respect of block 408 for FIG. 4A; the result of the determination of block 416 is metadata identifying the object-of-interest 502 depicted in the image data and the object-of-interest 502 represented in the non-image data as the same object-of-interest 502. Following block 408, the module 224 stores this metadata in the metadata storage 256.

In at least some example embodiments, the data analytics module 224 also determines from at least one of the image and non-image data whether the object-of-interest 502 satisfies an event threshold, and, when it does, indicates that the object-of-interest 502 has satisfied that threshold. The indicating may be done by displaying the tracking indicator, as discussed in respect of FIG. 4A; alternatively or additionally, the indicating may be done by doing at least one of displaying and sounding an event notification, such as a push notification on a computing device. The event threshold may take any one or more of a variety of forms. For example, the event threshold may be whether the object-of-interest 502 has moved a certain amount; has entered or left a certain area; or whether biometric readings are outside certain boundaries. More generally, the event threshold may be any of the behaviors that the system 100 may be trained to search for, as discussed above.

While FIGS. 5-10C described above describe the region being monitored by the system 100 as being the room 500, in different example embodiments a different type of region may be monitored. For example, any one or more of the devices 108,150 may monitor an outdoor region outside of a building. Instead of being mounted to walls, ceilings, or floors of the room 500, in at least some of those embodiments in which an outdoor region is monitored any one or more of the devices 108,150 may be body-worn, vehicle mounted, and/or mounted to building exteriors. These devices 108,150 may consequently be moving, stationary, or alternate between moving and stationary. For example, a building-mounted device 108,150 may be permanently stationary, whereas a vehicle-mounted device 108,150 or a body-worn device 108,150 may alternate between moving and stationary depending on the motion of the vehicle or person. The non-image capture devices 150 that are vehicle-mounted may comprise, for example, devices 150 that are not custom-mounted for use as part of the system 100; rather, they may comprise devices 150 that are found standard in many vehicles today, such as GPS sensors.

As additional examples, the image capture device may be body-worn or vehicle-mounted, and may comprise part of or be used in conjunction with nDOF sensors, wherein n is a suitable positive integer such as 3, 6, or 9.9DOF sensors may, for example, comprise a standalone sensor configured to measure nine degrees-of-freedom; alternatively, a 9DOF sensor may comprise multiple nDOF sensors having outputs that are fused together. Body-worn nDOF sensors may be used to measure acceleration of persons or cars, for example. Combining an nDOF sensor that allows an object-of-interest's 502 orientation to be known with a radio, cellular, or GPS device on that object-of-interest 502 that allows its location to be known may be used to determine the field-of-view of that object-of-interest 502. The system 100 may then map that determined field-of-view on to a map, and correlate it with known fields-of-view from one or more image capture and/or non-image capture devices 108,150 to display a field-of-view generated from data from the image capture and/or non-image capture devices 108,150 as the field-of-view of that object-of-interest 502. The fields-of-view of those image capture and/or non-image capture devices 108,150 may be manually mapped or automatically mapped based on nDOF sensors, such as 6DOF sensors.

Furthermore, the above-described embodiments are directed at correlating image data and non-image data. However, in at least some different example embodiments (not depicted), correlation may be done using only different types of image data, or using only different types of non-image data. For example, correlation analogous to that described in respect of blocks 408 and 416 may be done using multiple types of image data, such as thermal images captured using a thermal camera and visible light images captured using an RGB camera. Correlation of thermal and visible light images may be done using a convolutional neural network, for example, when the thermal and visible light images are substantially spatially correlated. Similarly, correlation analogous to that described in respect of blocks 408 and 416 may be performed using different types of non-image data, such as radar data and nDOF sensor data. Furthermore, the system 100 in certain example embodiments may correlate identical types of image data from the same type of image capture device 108 (e.g., thermal images captured using thermal cameras mounted at different locations); different types of image data from different types of image capture devices 108 (e.g., thermal images and visible light images, as described above); identical types of non-image data from the same type of non-image capture device 150 (e.g., radar data captured using radar sensors mounted at different locations); or different types of non-image data from different types of non-image captures devices 150 (e.g., radar data captured using a radar sensor and acceleration data captured using a 9DOF sensor).

Figure 11A:
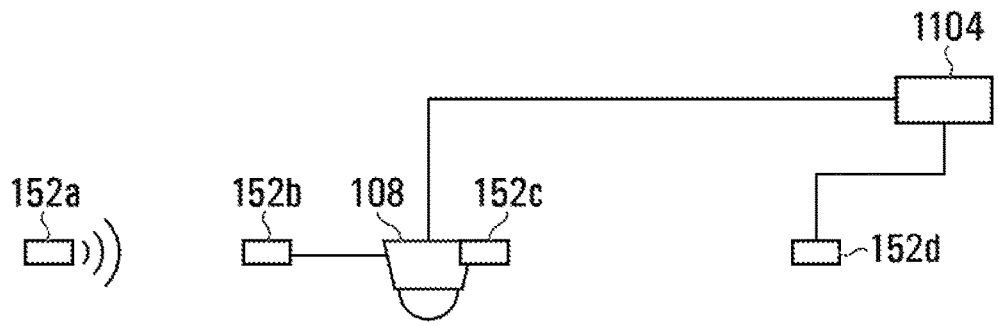
FIGS. 11A and 11B depict sensor groups in which an image capture device acts as a hub for one or more non-image sensors.
Figure 11B:
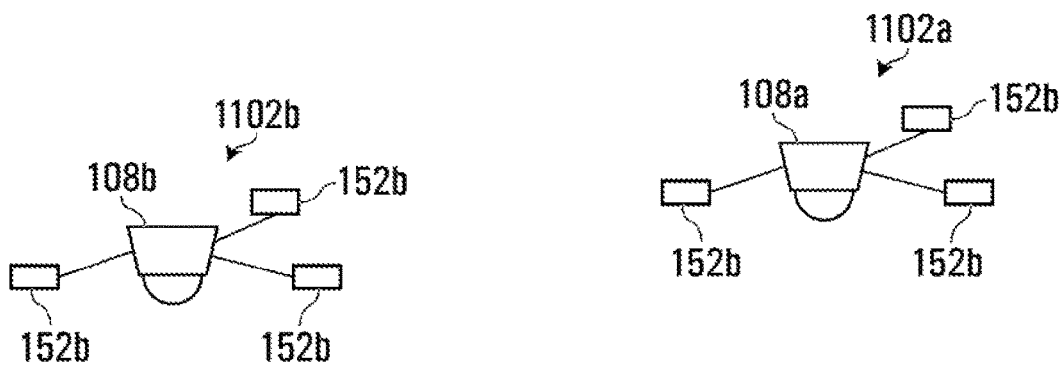

Referring now to FIGS. 11A and 11B, there are depicted image capture devices 108 that act as a hub for one or more sensors. FIG. 11A show a power-over-Ethernet (PoE) port 1104 that acts as both a power source and a means for communication to the portions of the system 100 not depicted in FIG. 11A. FIG. 11A also shows four types of non-image data sensors 152a-d: a standalone wired sensor 152d, which is wired to the PoE port 1104 and is powered by and communicates using that port 1104; a plug-in sensor 152c, which plugs into a socket in the device 108; a wired sensor 152b, which connects to the device 108 via a wired connection but does not otherwise directly physically contact the device 108; and a standalone wireless sensor 152a, which is battery powered and communicates wirelessly with the rest of the system 100. The wired sensor 152b and plug-in sensor 152c receive power and communicate via the device 108. In at least some different example embodiments (not depicted), a sensor may be connected to the device 108 and use the device 108 for only one of power and communication.

FIG. 11B depicts an example embodiment in which each of the first and the second image capture devices 108a,b acts as a hub for several wired sensors 152b. The first device 108a and the sensors 1110 connected to it collectively comprise a first sensor group 1102a, and the second device 108b and the sensors 1110 connected to it collectively comprise a second sensor group 1102b.

In embodiments in which one of the sensors 152 communicates with the rest of the system 100 via one of the image capture devices 108a,b, the data from that sensor 152 is communicated to the image capture device 108a,b prior to being processed by the rest of the system 100. For example, in an example embodiment in which thermal sensors 152 are being used to generate non-image data and they use one of the devices 108a,b as a hub, the thermal data from the sensors 152 is communicated to one of the devices 108a prior to the object-of-interest 502a-d imaged in that data being identified by the rest of the system 100. More generally, data from any non-image sensor 152 sent to the rest of the system 100 via one of the devices 108a,b is communicated to at least one of those devices 108a,b before the rest of the system 100 determines through correlation that the object-of-interest 502a-d depicted in the image data is the object-of-interest 502a-d identified in the non-image data. In at least some example embodiments, the devices 108a,b may use the data from the sensors 152 to enhance analytics or the present the data with camera footage for users to more easily understand the sensors' 152 output.

It is contemplated that any part of any aspect or embodiment discussed in this specification can be implemented or combined with any part of any other aspect or embodiment discussed in this specification.

The above discussed embodiments are considered to be illustrative and not restrictive, and the invention should be construed as limited only by the appended claims.

The invention claimed is:

1. A method comprising:
    receiving image data depicting an object-of-interest within a region and non-image data representing the object-of-interest within the region;
    determining that the object-of-interest depicted in the image data is the object-of-interest represented in the non-image data by correlating the image and non-image data;
    storing metadata identifying the object-of-interest depicted in the image data and the object-of-interest represented in the non-image data as the same object-of-interest;
    determining, using the non-image data, biometric metadata associated with the object-of-interest, the determining the biometric metadata including determining a rate-of-respiration of the object-of-interest;
    displaying, on a display, the biometric metadata, the image data depicting the object-of-interest that is associated with the biometric metadata, and an indication that the biometric metadata and the image data depicting the object-of-interest that is associated with the biometric metadata are associated;
    determining whether the rate-of-respiration is below a minimum threshold; and
    when the rate-of-respiration is below the minimum threshold, triggering a rate-of-respiration alarm, and
    wherein the object-of-interest is a person, and the non-image data includes position metadata collected from a radar sensor.

2. The method as claimed in claim 1 wherein the image data and the non-image data collectively represent the person at two locations at two different times, and further comprising displaying, on the display, a tracking indicator indicating that the person has moved between the two locations.

3. The method as claimed in claim 2 wherein the tracking indicator comprises a path indicator showing a path the person has traveled between the two locations.

4. The method as claimed in claim 1 wherein an image sensor that produces the image data is selected from the group consisting of a visible light sensor, a ultraviolet light sensor, an infrared light sensor, a near infrared light sensor, a short-wavelength infrared light sensor, a mid-wavelength infrared light sensor, and a long-wavelength infrared light sensor.

5. The method as claimed in claim 1 wherein the image data is of a field-of-view, the non-image data is of a scanning region, and the field-of-view and the scanning region do not overlap.

6. The method as claimed in claim 1 wherein the image data is of a field-of-view, the non-image data is of a scanning region, and the field-of-view and the scanning region overlap.

7. The method as claimed in claim 1 wherein the image and the non-image data are substantially spatially correlated, and correlating the image and the non-image data is performed using a convolutional neural network.

8. The method as claimed in claim 1 further comprising, prior to determining that the object-of-interest depicted in the image data is the object-of-interest represented in the non-image data by correlating the video and non-image data, receiving a signal to commence a search for the object-of-interest.

9. A method comprising:
    receiving image data depicting an object-of-interest within a region and non-image data representing the object-of-interest within the region;
    determining that the object-of-interest depicted in the image data is the object-of-interest represented in the non-image data by correlating the image and non-image data;
    storing metadata identifying the object-of-interest depicted in the image data and the object-of-interest represented in the non-image data as the same object-of-interest;
    determining biometric metadata associated with the object-of-interest, the determining the biometric metadata including determining a temperature of the object-of-interest;
    displaying, on a display, the biometric metadata, the image data depicting the object-of-interest that is associated with the biometric metadata, and an indication that the biometric metadata and the image data depicting the object-of-interest that is associated with the biometric metadata are associated;
    determining whether the temperature is within a temperature range; and when the temperature is outside of the temperature range, triggering a temperature alarm, and
wherein the object-of-interest is a person, and the image data includes thermal data.

10. The method as claimed in claim 9 wherein the image data is generated using a camera, the non-image data is generated using a non-image capture device, and the camera comprises a hub for the non-image capture device.

11. The method as claimed in claim 10 further comprising transmitting power to the non-image capture device via the hub.

12. The method as claimed in claim 9 wherein the non-image data is data contained in radiofrequency radiation.

13. The method as claimed in claim 12 wherein the radiofrequency radiation includes Bluetooth™ signals.

14. A method comprising:
receiving image data depicting an object-of-interest within a region and non-image data representing the object-of-interest within the region;
determining that the object-of-interest depicted in the image data is the object-of-interest represented in the non-image data by correlating the image and non-image data;
storing metadata identifying the object-of-interest depicted in the image data and the object-of-interest represented in the non-image data as the same object-of-interest, and
wherein the non-image data is generated using a radar sensor mounted to detect a crossing past a threshold distance from a doorway of a room, and the method further comprising:
using the non-image data from the radar sensor to determine when the object-of-interest has entered the room beyond the threshold distance; and
when the object-of-interest has entered the room beyond the threshold distance, incrementing a count of a number of persons in the room.

15. The method as claimed in claim 14 further comprising:
using the non-image data from the radar sensor to determine when the object-of-interest has transitioned from, relative to the doorway, being outside of the threshold distance to within the threshold distance; and
when the object-of-interest has transitioned, decrementing the count of the number of persons in the room.

16. A system comprising:
an image capture device;
a non-image capture device;
at least one processor communicatively coupled to the image and non-image capture devices; and
a memory communicatively coupled to the at least one processor and having stored thereon computer program code that is executable by the at least one processor, wherein the computer program code, when executed by the at least one processor, causes the at least one processor to perform a method comprising:
receiving image data depicting an object-of-interest within a region and non-image data representing the object-of-interest within the region;
determining that the object-of-interest depicted in the image data is the object-of-interest represented in the non-image data by correlating the image and non-image data;
storing metadata identifying the object-of-interest depicted in the image data and the object-of-interest represented in the non-image data as the same object-of-interest;
determining biometric metadata associated with the object-of-interest, the determining the biometric metadata including determining a temperature of the object-of-interest;
displaying, on a display, the biometric metadata, the image data depicting the object-of-interest that is associated with the biometric metadata, and an indication that the biometric metadata and the image data depicting the object-of-interest that is associated with the biometric metadata are associated;
determining whether the temperature is within a temperature range; and
when the temperature is outside of the temperature range, triggering a temperature alarm, and
wherein the object-of-interest is a person, and the image data includes thermal data.

17. The system as claimed in claim 16 wherein the image data is generated using a camera, the non-image data is generated using a non-image capture device, and the camera comprises a hub for the non-image capture device.

18. The system as claimed in claim 17 further comprising transmitting power to the non-image capture device via the hub.

19. The system as claimed in claim 16 wherein the non-image data is data contained in radiofrequency radiation.

20. The system as claimed in claim 19 wherein the radiofrequency radiation includes Bluetooth™ signals.

* * * * *